(12) United States Patent
Dai et al.

(10) Patent No.: US 10,463,460 B2
(45) Date of Patent: Nov. 5, 2019

(54) PERSONAL CLEANING CARE APPLIANCE

(71) Applicant: SHANGHAI SHIFT ELECTRICS CO., LTD., Shanghai (CN)

(72) Inventors: Xiaoguo Dai, Shanghai (CN); Zhenwu Xu, Shagha (CN); Ling Dai, Shanghai (CN)

(73) Assignee: SHANGHAI SHIFT ELECTRICS CO., LTD., Shanghai (CN)

(*) Notice: Subject to any disclaimer, the term of this patent is extended or adjusted under 35 U.S.C. 154(b) by 29 days.

(21) Appl. No.: 15/547,460

(22) PCT Filed: Jan. 28, 2015

(86) PCT No.: PCT/CN2015/071696
§ 371 (c)(1),
(2) Date: May 4, 2018

(87) PCT Pub. No.: WO2016/119136
PCT Pub. Date: Aug. 4, 2016

(65) Prior Publication Data
US 2018/0250107 A1 Sep. 6, 2018

(51) Int. Cl.
*A61C 17/34* (2006.01)
*A61C 17/22* (2006.01)
(Continued)

(52) U.S. Cl.
CPC ............ *A61C 17/221* (2013.01); *A61C 17/16* (2013.01); *A61C 17/34* (2013.01); *H02K 1/2786* (2013.01);
(Continued)

(58) Field of Classification Search
CPC ........ A61C 17/22; A61C 17/34; A61C 17/221
See application file for complete search history.

(56) References Cited

U.S. PATENT DOCUMENTS 7,067,945 B2 6/2006 Grez et al.
2002/0084707 A1 7/2002 Tang
(Continued)

FOREIGN PATENT DOCUMENTS

CN 1792023 A 6/2006
CN 001792023 A 6/2006
(Continued)

OTHER PUBLICATIONS

Extended European Search Report dated Sep. 6, 2018, ten (10) pages, European Patent Office.
(Continued)

*Primary Examiner* — Michael D Jennings

(57) ABSTRACT

A cleaning care appliance comprises a transducer comprising a drive shaft and magnets arranged on the left and right sides of the longitudinal axis of the drive shaft. The magnets are independent of each other, the polarity of the magnetic pole of one side of the magnet is opposite to that of the other side in the direction facing driving coil, the angle between the direction of magnetic force lines inside the magnets and the direction of the longitudinal axis of driving coil iron core is greater than 45° and smaller than 135°, the magnets move with respect to the elastic element retainer. When alternating current flows through the drive coil, the angle between magnet movement direction and the longitudinal axis of the core is greater than 170° and smaller than 190°. The appliance has low cost, low noise, low damping, and is safe, and reliable.

23 Claims, 16 Drawing Sheets

(51) Int. Cl.
*A61C 17/16* (2006.01)
*H02K 33/02* (2006.01)
*H02K 33/18* (2006.01)
*H02K 7/10* (2006.01)
*H02K 1/27* (2006.01)
*H02K 1/34* (2006.01)
*H02K 7/09* (2006.01)

(52) U.S. Cl.
CPC ............... *H02K 1/34* (2013.01); *H02K 7/09* (2013.01); *H02K 7/10* (2013.01); *H02K 33/02* (2013.01); *H02K 33/18* (2013.01); *A46B 2200/1006* (2013.01); *A46B 2200/1033* (2013.01); *A46B 2200/1066* (2013.01)

(56) References Cited

U.S. PATENT DOCUMENTS

| 2003/0204924 | A1 | 11/2003 | Grez et al. | |
|---|---|---|---|---|
| 2016/0100923 | A1* | 4/2016 | Lee | A61C 17/3418 15/22.1 |
| 2016/0143430 | A1* | 5/2016 | Davidov | A46B 15/0024 15/22.1 |
| 2016/0183670 | A1* | 6/2016 | Brewer | A46B 9/021 15/22.1 |
| 2016/0192769 | A1* | 7/2016 | Bloch | A46B 15/0012 15/22.1 |

FOREIGN PATENT DOCUMENTS

| CN | 101541258 A | 9/2009 |
|---|---|---|
| CN | 102545526 A | 7/2012 |
| CN | 203674948 U | 6/2014 |
| CN | 203674949 U | 6/2014 |
| CN | 203827149 | 9/2014 |
| CN | 104617732 A | 5/2015 |
| CN | 204392053 U | 6/2015 |
| JP | 2003210495 A | 7/2003 |
| JP | 2005525067 A | 8/2005 |
| JP | 2010005043 A | 1/2010 |
| JP | 2010125263 A | 6/2010 |
| JP | 2013118779 A | 6/2013 |
| WO | 0241332 | 5/2002 |

OTHER PUBLICATIONS

Korean Office Action dated Dec. 17, 2018 for Application No. 10-2017-7021222.

\* cited by examiner

PERSONAL CLEANING CARE APPLIANCE

CROSS-REFERENCE TO RELATED APPLICATION(S)

This application is the National Stage of International PCT Application No. PCT/CN2015/071696 filed on Jan. 28, 2015 and is herein incorporated by reference in its entirety.

TECHNICAL FIELD

The present invention relates to an appliance for personal cleaning and care, and more specifically, to a personal cleaning care appliance, such as an electric toothbrush, an electric shaver, an electric face cleansing instrument, an electric shower and the like.

BACKGROUND

For personal cleaning care appliances, such as the electric toothbrush, the electric shaver, the electric face cleansing instrument, the electric shower and the like, it is important to have a personal cleaning care appliance which can convert the reciprocating motion into a desired rotary motion of a cleaning element, and these personal cleaning care appliances should be simple in structure, convenient to assemble, long in service life, and safe and reliable.

There are known a number of driver configurations for driving the cleaning elements, such as motors, magnetic systems and electromagnetic systems. Some driver configurations employ bearings (such as ball bearings) to support the driver, and such configurations are both expensive and complicated, and also have noise and motor damping.

CN 100591301C discloses a device for converting a lateral motion into a rotary motion of the work piece of the appliance, wherein the drive assembly comprises an electromagnet which is capable of generating a lateral force and engages with two permanent magnets in operation, and the permanent magnets are fixed to the moveable end pieces located at the rear end of the motion conversion assembly, so as to move the end piece in a side-to-side slightly arcuate translation manner. The two permanent magnets are relatively fixedly mounted onto the end pieces. The motion conversion assembly converts the driving action of the drive assembly into a twisting or rotating action of the drive shaft through the provision of a leaf spring, and the drive shaft then rotates the brush head arm and the brush head such that they rotate around the longitudinal axis of the drive shaft. CN 101297775B discloses a method for adjusting the elastic elements of a resonant driving system, wherein the spring elements are not curved, and their resonant frequency is changed by sufficiently altering the stiffness of the elastic elements so that the resonant vibration frequency is very close to the driving frequency of the appliance.

SUMMARY

The technical problem to be solved by the present invention is to provide a personal cleaning care appliance which has a simple and compact structure, low cost, easy assembly, smooth rotation, low noise, low damping, and is safe and reliable.

In order to solve the above technical problem, the present invention provides a personal cleaning care appliance comprising: a handle comprising a handle housing, a power supply portion provided inside the handle housing for supplying power to respective portions of the personal cleaning care appliance, a control portion provided inside the handle housing for controlling the various operation modes of the personal cleaning care appliance and the opening or closing of the personal cleaning care appliance, a trigger portion provided inside the handle housing for turning on or off an operation of the personal cleaning care appliance, and a driver provided inside the handle housing for converting an input electrical energy into an output mechanical energy, wherein the driver comprises a transducer, a drive coil, a drive coil iron core arranged in the drive coil, and a left driver bracket and a right driver bracket for supporting the driver; a cleaning assembly comprising a cleaning element carrier and cleaning elements distributed on the cleaning element carrier, wherein the cleaning assembly is detachably connected to a drive shaft; wherein the transducer comprises a drive shaft inserted into the cleaning assembly, at least one transducer elastic element retainer fastened to the left and right driver brackets, at least two permanent magnets disposed on left and right sides with respect to a longitudinal axis of the drive shaft, corresponding permanent magnet brackets for fixedly connecting the permanent magnets, left and right transducer transmission arms fixedly connected to the permanent magnet brackets and to the drive shaft, and at least two left and right transducer elastic elements disposed on the left and right sides of the longitudinal axis of the drive shaft. One end of the left transducer elastic element and one end of the right transducer elastic element are fixedly connected to the transducer elastic element retainers respectively, and the other end of the left transducer elastic element and the other end of the right transducer elastic element are fixedly connected to the corresponding transducer transmission arms respectively; wherein the permanent magnets are independent from each other; a polarity of a magnetic pole of the left permanent magnets in a direction toward the drive coil is S pole or N pole; a polarity of a magnetic pole of the right permanent magnets in a direction toward the drive coil is opposite to the polarity of the magnetic pole of the left permanent magnets; the left and right permanent magnets are arranged such that an angle between a direction of their inner magnetic line and a direction of the longitudinal axis of the drive coil iron core is greater than 45° and less than 135° respectively; the left and right permanent magnets are movable relative to the transducer elastic element retainers; when an alternating current passing through the drive coil has a frequency f0, a movement direction of the left and right permanent magnets is approximately parallel with the direction of the longitudinal axis of the drive coil iron core, that is, the angle therebetween is greater than 170° and less than 190°, or greater than −10° and less than 10°.

The above technical solution has beneficial technical effects in the following two aspects. In the first aspect, when the left and right permanent magnets are arranged such that the angle formed between the direction of their inner magnetic line and the direction of the longitudinal axis of the drive coil iron core is greater than 45° and less than 135°, the direction of the magnetic line passing through the drive coil formed between the left and right permanent magnets and the direction of the magnetic line within the coil formed by the energized drive coil intersect spatially at an angle greater than 45° and less than 135°, that is to say, the mutual interference between the axis of the magnetic field generated by the drive coil and the axis of the permanent magnetic field is weak. That is, the above two magnetic fields have weak mutual interference; when the magnitude and direction of the current in the drive coil varies, the magnetic field generated in the drive coil could vary correspondingly, however, due to the weak interference between the axis of the magnetic field of the drive coil and the axis of the permanent magnetic field, the variation of the magnetic field generated in the drive coil has a highly limited influence upon the permanent magnetic field. When alternating current passing through the drive coil varies according to cosine, due to the energized conductor being in the permanent magnetic field, the energized conductor is subjected to the electromagnetic force, and the electromagnetic force formula is F=NBIL cos ωt, where B is the magnetic field density of the permanent magnetic field at the conductor, I cos ωt is the current flowing through the conductor, L is the effective length of the conductor in the permanent magnetic field, N is the total number of the conductor, ω is the electrical angular speed at which the current varies, t is time. It is known from the electromagnetic force formula that, if N, B, and L keep unchanged, then F merely depends on I cos ωt. The above two magnetic fields having weak mutual interference can ensure that B has a smaller variation, and the internal structure of the cleaning appliance can ensure that the N and L keep unchanged. Since the cos ωt curve is a smooth curve, that is to say, the electromagnetic force is a continuous gradient physical quantity without an abrupt change, thereby ensuring that the cleaning appliance achieves a smooth non-impact motion under the driving of the electromagnetic force F, that is, the acceleration of the motion has no abrupt change. In a second aspect, the present invention creatively introduces at least two transducer elastic elements, namely the left and right transducer elastic elements, respectively; the bending strain of the elastic material is utilized to form a transducer having a natural-vibration frequency $f_{natural}$; when the natural frequency $f_{natural}$ of the transducer is very close to the driving frequency f0, the electromagnetic force generated by the drive coil in the handle housing and acting on the transducer causes the transducer to be in a resonance oscillation state, and when the natural frequency $f_{natural}$ of the transducer is equal to the driving frequency f0, the electromagnetic force generated by the drive coil in the handle housing and acting on the transducer causes the transducer to be in a resonant vibration state. It is well known that the energy transfer efficiency in the resonance oscillation state or the resonant vibration state is very high. In an existing driver configuration using a bearing (e.g., a ball bearing), a restraining piece such as a bearing is provided to prevent other motions of the cleaning device in addition to the rotary motion; however, such a constraint will bring noise and energy loss, which also increases the cost. In the present invention, due to the reasonable configuration of the elastic elements and the permanent magnets, it is possible to achieve a smooth rotation of the transducer, thus eliminating some of the restraining pieces (such as bearings, etc.) that must be provided in order to achieve the rotation of the cleaning appliance. Since the reasonable configuration of the permanent magnet causes the electromagnetic resultant force on the transducer to be approximately zero, and the torque acting on the transducer is handily used so that the restraining structure can be removed, the cleaning appliance has a more compact structure, a smoother rotation, and a weaker noise. Furthermore, compared with the structure in which only one transducer elastic element is provided, the structure of the cleaning appliance according to the present invention has a weaker noise and higher efficiency. To sum up the above two aspects of beneficial technical effects, the present invention realizes the objectives of simple and compact structure, low cost, convenient assembling, smooth rotation, low noise, low damping and being safe and reliable.

Preferably, the left and right permanent magnets are arranged such that the angle between the direction of their inner magnetic line and the direction of the longitudinal axis of the drive coil iron core is 90°. By this time, the direction of the magnetic line passing through the drive coil formed between the left and right permanent magnets of the present invention and the direction of the magnetic line within the coil formed by the energized drive coil intersect spatially at 90°, that is to say, the axis of the magnetic field generated by the drive coil and the axis of the permanent magnetic field are orthogonal to each other. The orthogonality of the above two magnetic fields can be understood as the fact that the two magnetic fields do not interfere with each other; when the magnitude and direction of the current in the drive coil varies, the magnetic field generated by the drive coil will change correspondingly; however, due to the orthogonality of the axis of the magnetic field of the drive coil to the axis of the permanent magnetic field, the magnetic field variation generated by the drive coil does not affect the permanent magnetic field. When alternating current passing through the drive coil varies according to cosine, due to the energized conductor being in the magnetic field of the permanent magnet, the energized conductor is subjected to the electromagnetic force, and the electromagnetic force formula is F=NBIL cos ωt, where B is the magnetic field density of the permanent magnetic field at the conductor, I cos ωt is the current flowing through the conductor, L is the effective length of the conductor in the permanent magnetic field, N is the total number of the conductor, ω is the electrical angular speed at which the current varies; t is time. It is known from the electromagnetic force formula that, if N, B and L keep unchanged, then F merely depends on I cos ωt. In this case, the above orthogonal magnetic fields can ensure that B does not change, and the internal structure of the cleaning appliance can also ensure that N and L keep unchanged. Since the cos ωt curve is a smooth curve, that is to say, the electromagnetic force is a continuous gradient physical quantity without an abrupt change, thereby ensuring that the cleaning appliance achieves a smooth non-impact motion under the driving of the electromagnetic force F, that is, the acceleration of the motion has no abrupt change.

Preferably, in the personal cleaning care appliance of the present invention, the portion of the transducer, in which the left transmission arm, the left permanent magnet located at the same side as the transmission arm with respect to the longitudinal axis of the drive shaft, and the corresponding permanent magnet bracket are in fixed connection, and which is below the left transducer elastic element located at the same side as the transmission arm with respect to the longitudinal axis of the drive shaft, is defined as a lower left portion of the transducer; the portion of the transducer, in which the right transmission arm, the right permanent magnet and the corresponding permanent magnet bracket are in fixed connection, and which is below the right transducer elastic element, is defined as a lower right portion of the transducer; at least one gap (two gaps in the present invention) exists between the lower left portion of the transducer and the lower right portion of the transducer; in the gap(s) there exits a magnetic field force sufficient to compensate for a translation of the transducer due to non-equilibrium forces, and at least one permanent magnet is allowed to move relative to the other permanent magnet having the opposite polarity. This technical solution fully takes account the fact that, in the past personal cleaning appliance, due to the manufacturing errors or other interference factors, the magnitude of each set of magnetic field forces are caused to be unequal, thereby destroying the equilibrium condition of forces experienced by the transducer of the personal cleaning care appliance, and the transducer experiencing non-equilibrium forces will generate a translation tendency other than its rotary motion, thereby losing energy and producing the noise. Therefore, such a technical solution can employ the two gaps, and by changing the distance of the gaps, the above non-equilibrium forces can be effectively corrected and then the motion of the personal cleaning care appliance can be made smoother and more stable.

Preferably, the gap between the lower left portion of the transducer and the lower right portion of the transducer has a length of 0.1 mm to 2 mm. More preferably, the length of the gap is 0.2 mm to 1 mm. Hence, it is possible to more effectively make full use of the function of the gaps for adjusting the non-equilibrium forces, so as to better correct the above non-equilibrium forces, and further to make the motion of the personal cleaning care appliance smoother and more stable.

Preferably, the permanent magnets of the present invention are rectangular parallelepiped NdFeB permanent magnets, preferably being about 5 mm to 30 mm in length, about 2 mm to 20 mm in width, and about 1 mm to 10 mm in height. This kind of permanent magnet has the advantages of convenient processing and high degree of normalization and standardization, and it is easy to be put into industrial production. At the same time, different sizes of this kind of permanent magnets can be employed according to the different sizes of personal cleaning care appliances, so as to meet the requirements of different types of personal cleaning care appliances.

Preferably, the transducer can also be provided with four permanent magnets, and the left permanent magnets and right permanent magnets are arranged such that the reaction forces which they are subjected to are of approximately equal magnitude, the magnitude difference is approximately less than 10%, the directions of the reaction forces are approximately opposite, and the angle between the directions is less than 10°. Hence, the drive shaft is subjected to an approximately alternating equilibrium force, and the alternating equilibrium force generates an alternating torque, thus causing a high-speed reciprocating and high effective rotation of the drive shaft.

Preferably, the transducer elastic elements comprise rectangular elastic elements or sheet type elastic elements. The rectangular elastic element or the sheet type elastic element has advantages of better versatility, convenient processing, low price, easy availability and replaceability, as well as a favorable service life, and they can reliably and continuously absorb and release energy, in order to ensure the normal and smooth operation of the personal cleaning care appliance.

Preferably, the transducer may be provided with two transducer elastic elements distributed symmetrically at the left and right sides of the longitudinal axis of the drive shaft, and the angle of the two transducer elastic elements is 180°; the left and right transducer elastic elements are set in such a way that the left transducer elastic element and the right transducer elastic element are approximately equal in their lengths and their bending resistant section factors (or section modulus in bending) respectively with a magnitude difference less than 10%, such that the deflection of the left transducer elastic element and the deflection of the right transducer elastic element have approximately equal magnitudes with a magnitude difference less than 10%, and are opposite in directions. Hence, the drive shaft is subjected to an approximately alternating equilibrium force, and the alternating equilibrium force generates an alternating torque, thus causing a high-speed reciprocating and high effective rotation of the drive shaft.

More preferably, the number of the transducer elastic elements may be plural, and particularly, the transducer may also be provided with three transducer elastic elements, in which two of the transducer elastic elements form an angle $2\alpha$, $0°<\alpha<90°$, and either of the two transducer elastic elements forms an angle $\delta$ with the third transducer elastic element, $\delta=(360°-2\alpha)/2$. With such an optimized technical solution, it is possible to make the difference of the magnitudes of the forces of the left and right transmission arms of the transducer respectively acting on the drive shaft to be less than 10%, and to make the directions of the forces to be opposite; and the moments of the left and right transmission arms to the longitudinal axis of the drive shaft are approximately equal in magnitude and identical in direction, and thereby the drive shaft is allowed to drive the cleaning element carrier and the cleaning elements to achieve a smooth and high-speed reciprocating motion.

The personal cleaning care appliance comprises the electric toothbrush, the electric shaver, the electric face cleansing instrument, the electric shower, and it may also be other appliance having similar functions.

Figure 1:
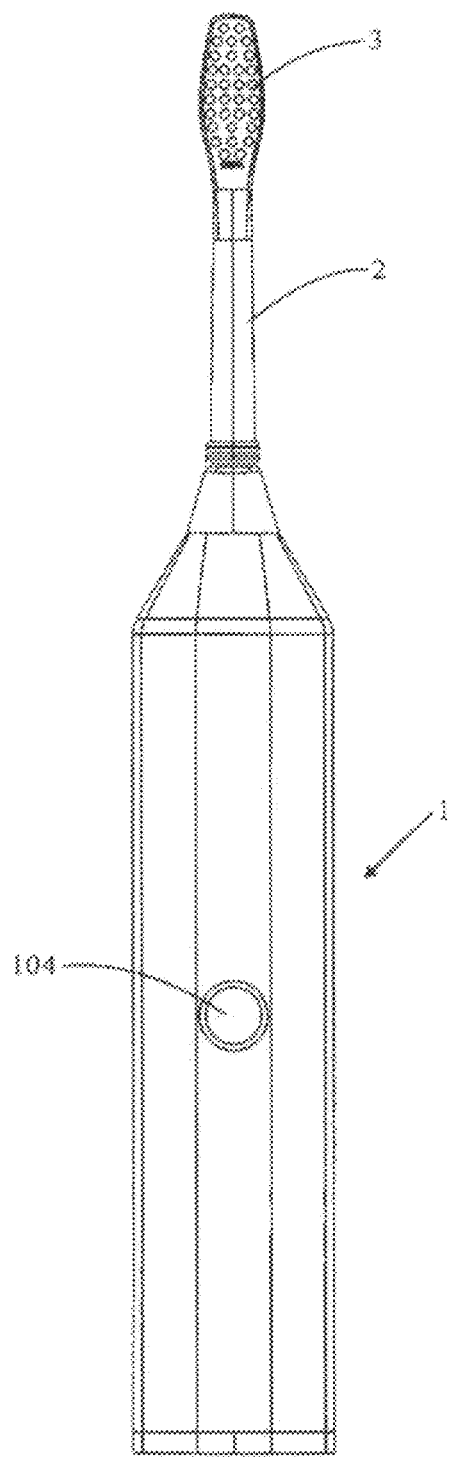
FIG. 1 is a front view of the personal cleaning care appliance of the present invention.

REFERENCE NUMERALS OF THE MAIN COMPONENTS 1 handle
2 cleaning element carrier 3 cleaning element
103 seal
104 switch button
105 handle housing
106 switch
107 circuit board of the control circuit
108 charge coil
109 rechargeable battery
110 driver
111 drive shaft
112 left driver bracket
113 right driver bracket
114 drive coil
115 drive coil iron core
116 left permanent magnet
117 right permanent magnet
118 left permanent magnet bracket
119 right permanent magnet bracket
120 left primary winding of the drive coil
121 right primary winding of the drive coil
122 left transducer elastic element
123 right transducer elastic element
124 the transducer elastic element retainers
125 left transmission arm of the transducer
126 right transmission arm of the transducer
127 fastening screw
128 secondary winding of the drive coil
129 lower gap between the lower left portion of the transducer and the lower right portion of the transducer
130 transducer
131 upper gap between the lower left portion of the transducer and the lower right portion of the transducer
211 drive shaft of the first variant of transducer
214 alternative drive coil of the first variant of transducer
215 alternative drive coil iron core of the first variant of transducer
216 upper left permanent magnet of the first variant of transducer
217 lower left permanent magnet of the first variant of transducer
218 lower right permanent magnet of the first variant of transducer
219 upper right permanent magnet of the first variant of transducer
222 left transducer elastic element of the first variant of transducer
223 right transducer elastic element of the first variant of transducer
224 transducer elastic element retainer of the first variant of transducer
225 left transmission arm of the first variant of transducer
226 right transmission arm of the first variant of transducer
227 upper left permanent magnet bracket of the first variant of transducer
228 lower left permanent magnet bracket of the first variant of transducer
229 upper right permanent magnet bracket of the first variant of transducer
230 lower right permanent magnet bracket of the first variant of transducer
231 secondary winding of the alternative drive coil of the first variant of transducer
232 left primary winding of the alternative drive coil of the first variant of transducer
233 right primary winding of the alternative drive coil of the first variant of transducer
234 upper gap between the lower left portion of the first variant of transducer and the lower right portion of the first variant of transducer
235 lower gap between the lower left portion of the first variant of transducer and the lower right portion of the first variant of transducer
311 drive shaft of the second variant of transducer
314 alternative drive coil of the second variant of transducer
315 alternative drive coil iron core of the second variant of transducer
316 upper left permanent magnet of the second variant of transducer
317 lower left permanent magnet of the second variant of transducer
318 lower right permanent magnet of the second variant of transducer
319 upper right permanent magnet of the second variant of transducer
322 left transducer elastic element of the second variant of transducer
323 right transducer elastic element of the second variant of transducer
324 left transducer elastic element retainer of the second variant of transducer
325 right transducer elastic element retainer of the second variant of transducer
326 left transmission arm of the second variant of transducer
327 right transmission arm of the second variant of transducer
328 upper left permanent magnet bracket of the second variant of transducer
329 lower left permanent magnet bracket of the second variant of transducer
330 upper right permanent magnet bracket of the second variant of transducer
331 lower right permanent magnet bracket of the second variant of transducer
332 upper gap between the lower left portion of the second variant of transducer and the lower right portion of the transducer
333 lower gap between the lower left portion of the second variant of transducer and the lower right portion of the transducer
334 gap between the left transmission arm of the second variant of transducer and the right transmission arm of the transducer
401 first transducer elastic element
402 second transducer elastic element
403 third transducer elastic element

DETAILED DESCRIPTION

Hereinafter, an exemplary embodiment of the present invention will be described in more detail with reference to a typical example of an electric toothbrush as a personal cleaning care appliance in conjunction with the accompanying drawings. Although only the electric toothbrush is used as an example, the present invention is not limited thereto. The present invention may also be applicable to the electric shaver, the electric face cleansing instrument, the electric shower and similar appliances used for personal cleaning and care.

Similar reference numerals refer to similar parts throughout the drawings.

For the sake of clarity, this description uses the terms for expressing spatial relative location, such as "up", "down", "upper", "lower", "left", "right", "transverse", "forward", "opposite" and the like to briefly describe the relationships between one element or feature and another element (s) or feature (s) as shown in the figures, wherein the direction of the longitudinal axis of the drive coil means the direction of the magnetic line generated in the iron core when current flows in parallel with the drive coil; the terms "up", "down", "upper", "lower" are relative to the longitudinal axis of the drive shaft, where the upward direction parallel with the longitudinal axis of the drive shaft when facing corresponding figures is defined as "up", "upper", and the downward direction parallel with the longitudinal axis of the drive shaft is defined as "down", "lower"; the terms "left" and "right" are relative to the longitudinal axis of the drive shaft, where the left side of the longitudinal axis of the drive shaft in the direction perpendicular to the longitudinal axis of the drive shaft when facing corresponding figures is defined as "left", and its right side is defined as "right"; the term "transverse" refers to the direction perpendicular to the longitudinal axis of the drive shaft; "outward" means the direction perpendicular to the paper surface while facing the operator; "inward" means the direction perpendicular to the paper surface away from the operator.

In addition, the word "and/or" used in the present application comprises any one and all combinations of one or more of the listed associated words.

Although this description uses the words "first" and the like to describe a plurality of elements or component parts, these elements or component parts shall not be limited by these words. These words are used only to distinguish between one element or component part and another element or component part, instead of comprising "being in sequence". Therefore, even if the ordinal words of those elements or component parts discussed below are to be transformed from each other, the examples do not go beyond the conception and scope of the present invention.

Figure 2:
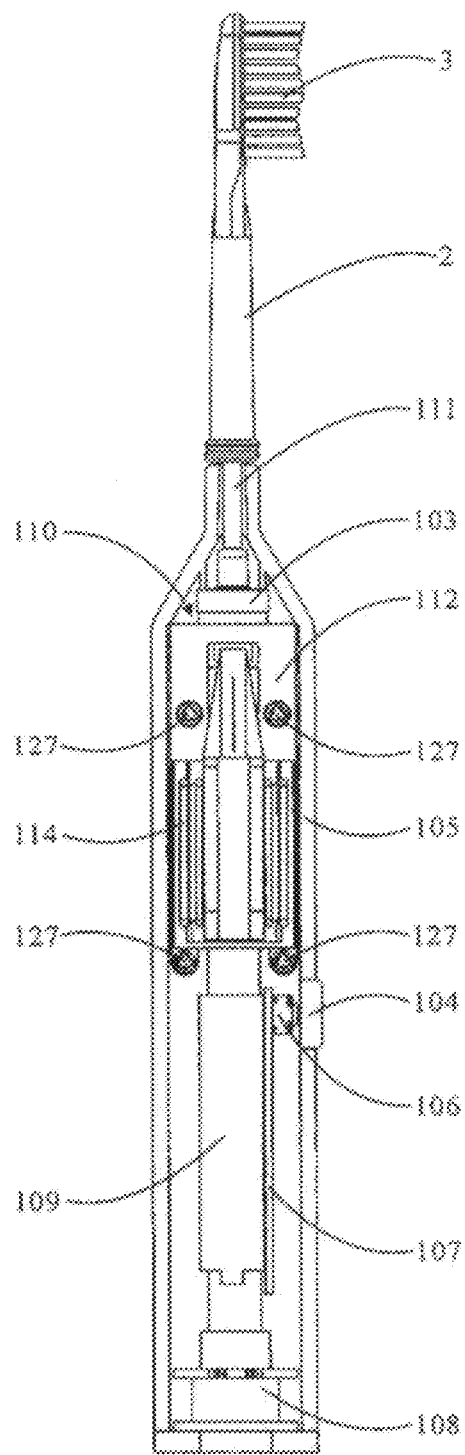
FIG. 2 is a lateral partial sectional view of the personal cleaning care appliance shown in FIG. 1.

As an example, also as shown in FIGS. 1 and 2, the personal cleaning care appliance, such as the electric toothbrush and the like, comprises a handle 1 and a cleaning assembly detachably (e.g., in a snap-fit manner) mounted onto the handle 1. The handle 1 comprises a handle housing 105. The cleaning assembly comprises a cleaning element carrier 2, and cleaning elements 3 distributed on the cleaning element carrier 2, wherein the cleaning elements 3 may be an article, such as bristles. The cleaning assembly (e.g., a brush head) is detachably coupled with the drive shaft 111 by the cleaning assembly, for example, in a snap-fit manner, and the snap-fitting may allow the drive handle 1 and the cleaning assembly to be reliably coupled together, and it is also possible to conveniently separate the drive handle 1 from the cleaning assembly.

A power supply portion, a control portion, a trigger portion and a driver are provided inside the handle housing 105. Ordinarily, the power supply portion comprises a rechargeable battery 109 and a charging circuit for supplying power to respective portions of the appliance; the control portion comprises a circuit board 107 of the control circuit for controlling the various operation modes of the electric toothbrush and the opening or closing of the electric toothbrush, and so on; the trigger portion comprises a switch 106 for turning on and off the operation of the electric toothbrush; the driver functions to convert input electrical energy into output mechanical energy. The handle 1 further comprises: a charge coil 108, a rechargeable battery 109, a circuit board 107 of the control circuit, which are mounted in the handle housing 105; a switch 106 mounted on the circuit board 107 of the control circuit; a switch button 104 attached to the handle housing 105; a driver 110 fixed in the handle housing 105; and a seal 103. The circuit board 107 of the control circuit is in electrical communication with the switch 106 and the driver 110. The switch button 104 is coupled with the switch 106 so as to actuate the switch 106 by operating the switch button 104. One end of the seal 103 is coupled with the cleaning element carrier 2, and the other end of the seal 103 is coupled with the driver 110 for use as a waterproof seal.

Figure 3:
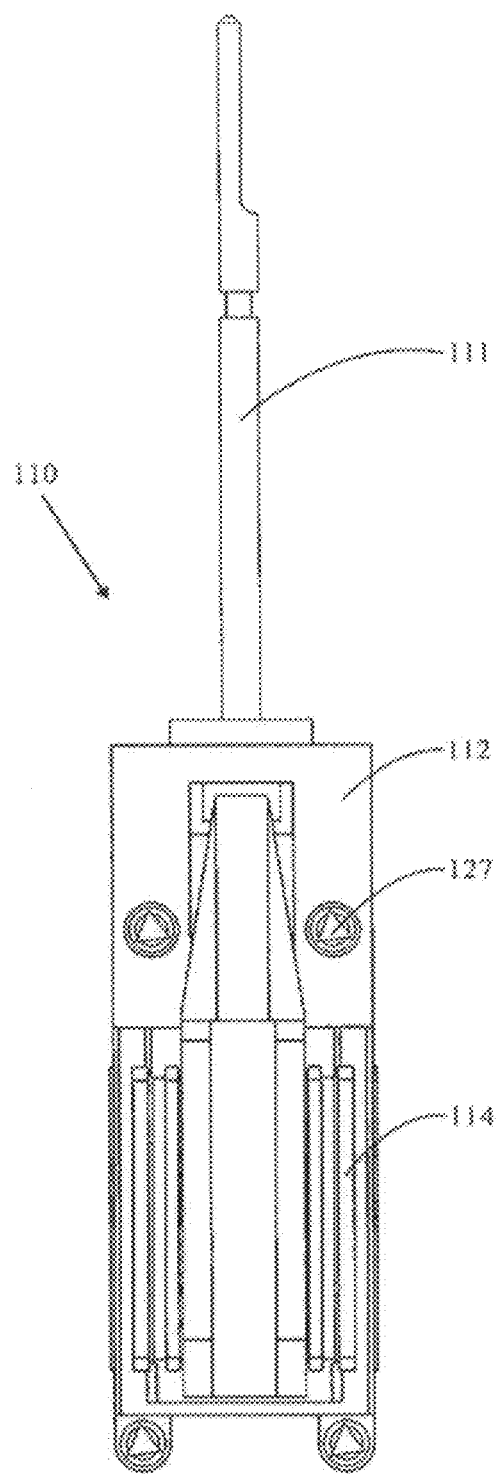
FIG. 3 illustrates a front view of the driver shown in FIG. 2.
Figure 4:
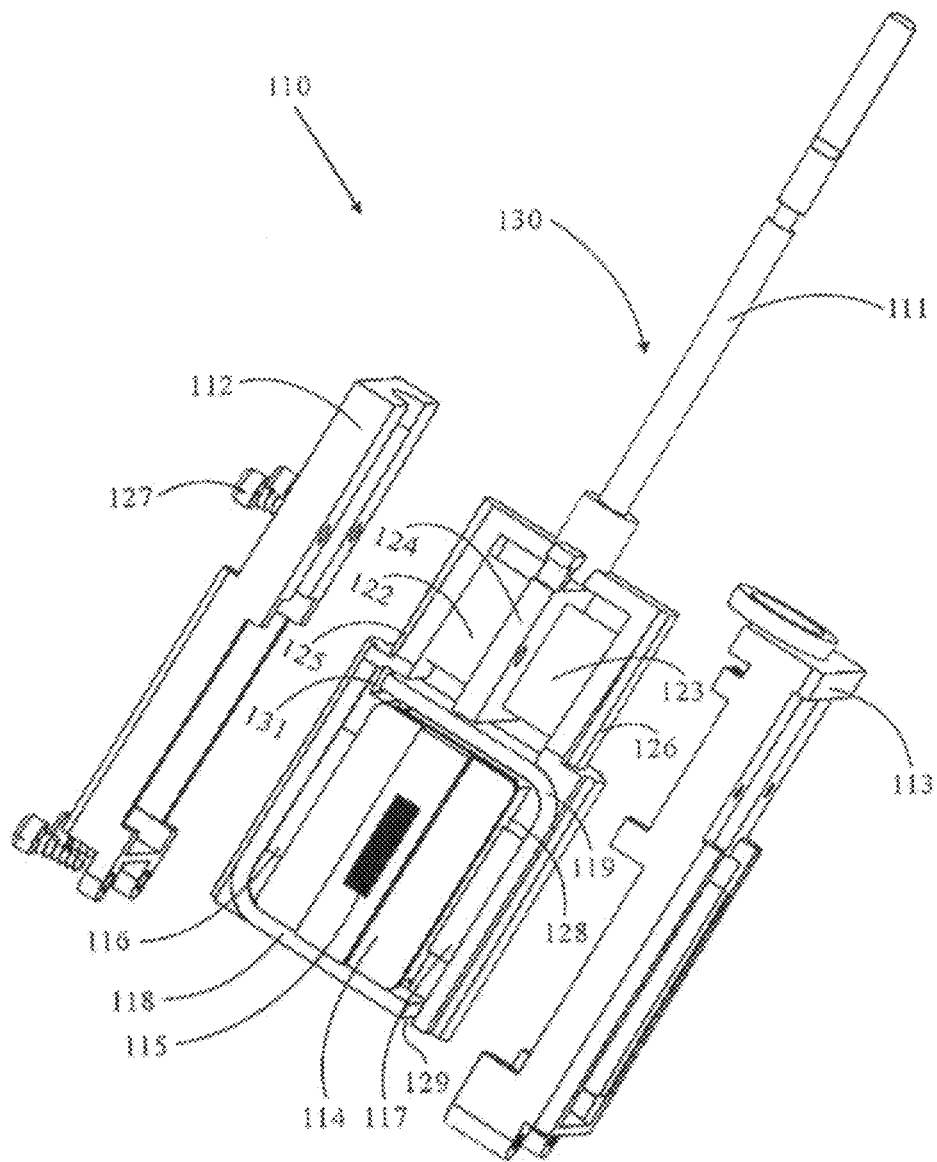
FIG. 4 is an exploded view of the driver shown in FIG. 3.

As shown in FIGS. 3 and 4, the driver 110 comprises a transducer 130, a drive coil 114, a drive coil iron core 115 having a high magnetic permeability characteristic and arranged in a hollow portion of the drive coil 114 in a direction perpendicular to the longitudinal axis of the drive shaft, a left driver bracket 112 and a right driver bracket 113 for supporting the driver 110, and a fastening screw 127, wherein the left and right driver brackets 112, 113 are fastened together with the transducer elastic element retainer 124 of the transducer 130 through the fastening screw 127.

The transducer 130 comprises a drive shaft 111, a transducer elastic element retainer 124, the left transducer elastic element 122 and the right transducer elastic element 123 respectively located at the left and right sides of the longitudinal axis of the drive shaft, left and right transmission arms 125 and 126 of the transducer, left and right permanent magnets 116 and 117, and left and right permanent magnet brackets 118 and 119. The angle formed between the left and right transducer elastic elements 122 and 123 may be 180°. The left and right transducer elastic elements 122, 123 may be coupled together with the transducer elastic element retainer 124 through injection molding, and it may also be that a single piece of elastic element is molded with the transducer elastic element retainer 124 through injection molding. In the overall injection molding solution, although the left and right transducer elastic elements 122, 123 are made using a single piece of elastic element, since directions of the forces acting on the left and right transducer elastic elements 122, 123 are different, it still can be considered to be composed of two elastic elements.

Absolutely, the transducer elastic element may have other arrangement modes, which will also fall within the scope of the present invention.

The cleaning assembly is detachably inserted into the drive shaft 111 so that the transducer 130 is coupled together with the cleaning assembly. One end of the left transducer elastic element 122 and one end of the right transducer elastic element 123 are fixedly connected together to the transducer elastic element retainer 124 respectively, and the other end of the left transducer elastic element 122 and the other end of the right transducer elastic element 123 are fixedly connected together with the left and right transmission arms 125, 126 of the transducer respectively. The left and right permanent magnets 116, 117 and left and right permanent magnet brackets 118, 119 of the transducer 130 are fixedly coupled with the left and right transducer elastic elements 122, 123, the left and right transmission arms 125, 126 of the transducer, the drive shaft 111 and the transducer elastic element retainer 124. The transducer elastic element retainer 124 is fixedly coupled with the left and right driver brackets 112, 113 through a fastening screw 127 and is fixed to the handle 1. The above parts may be injection molded into one piece, and may also be assembled together in a mechanical joint manner.

The left and right permanent magnets 116 and 117 of the transducer 130 enclose a hollow zone with the left and right permanent magnet brackets 118 and 119. The hollow zone is used to house the drive coil 114 and the drive coil iron core 115. The portion of the transducer, in which the left transmission arm 125, the left permanent magnet 116 and the left permanent magnet bracket 118 are fixedly coupled together, and which is below the left transducer elastic element 122, is referred to as the lower left portion of the transducer. The portion of the transducer, in which the right transmission arm 126, the right permanent magnet 117 and the right permanent magnet bracket 119 are fixedly coupled together, and which is below the right transducer elastic element 123, is referred to as the lower right portion of the transducer. At least one gap, generally two gaps 129 and 131, exists between the lower left portion of the transducer and the lower right portion of the transducer. Such a gap may allow at least one left permanent magnet 116 to move relative to a right permanent magnet 117 having opposite polarity. The gap enables the left and right permanent magnets 116 and 117 to be independent of each other. The transducer 130 is provided with a drive shaft 111 along the direction adjacent to the cleaning assembly; the drive shaft 111 and the cleaning assembly are detachably assembled together, and by reasonably designing the shape of the drive shaft 111, the drive shaft 111 can effectively transfer the motion and energy to the cleaning assembly.

The motion analysis is carried out below in conjunction with the transducer 130. Referring to FIGS. 1 to 7, when the user triggers the switch button 104 of the electric toothbrush to thereby trigger the switch 106, the control system in the handle 1 initiates the drive coil 114, and alternating current at a frequency of f0/2 alternately passes through the left primary winding 120 and the right primary winding 121 of the drive coil 114. The magnetic field generated by the left permanent magnet 116 and the right permanent magnet 117 of the transducer 130 interacts with the energized drive coil 114 to generate an electromagnetic force. By reasonably disposing the permanent magnets 116, 117 relative to the drive coil 114, the electromagnetic force received by the transducer 130 is essentially in equilibrium, and the torque M is generated. Due to alternating current flowing through the drive coil 114, the torque M on the transducer 130 also has an alternating direction. Assume that in the initial state, the direction of the torque M of the transducer is clockwise. Since the transducer elastic element retainer 124 is fixed at the left and right driver brackets 112, 113, the left transmission arm 125 of the transducer drives the left transducer elastic element 122 to bend in the clockwise direction, the left transducer elastic element 122 undergoes a bending strain, stores energy, and the left transducer elastic element 122 undergoes bending strain around the transducer elastic element retainer 124 in the clockwise direction. At the same time, the right transmission arm 126 of the transducer drives the right transducer elastic element 123 to bend in the clockwise direction, the right transducer elastic element 123 undergoes bending strain, and stores energy, and the right transducer elastic element 123 also undergoes bending strain around the transducer elastic element retainer 124 in the clockwise direction. Therefore, the transducer 130 reciprocally rotates in response to the driving from the drive coil 114 in the housing 105 of the handle 1. The cleaning element 3 is coupled to the transducer 130 through the cleaning element carrier 2, and the transducer 130 drives the cleaning element 3 to reciprocally rotate.

In this embodiment, at least two transducer elastic elements, namely, the left transducer elastic element 122 and the right transducer elastic element 123, are creatively introduced, respectively, and the bending strain of the elastic material is utilized so as to constitute the transducer 130 having a natural-vibration frequency $f_{natural}$; when the natural frequency $f_{natural}$ of an the transducer 130 is very close to the driving frequency f0, the electromagnetic force generated by the drive coil 114 in the handle housing 105 acts on the transducer 130 to cause the transducer 130 to be in a resonance oscillation state, and when the natural frequency $f_{natural}$ of the transducer 130 is equal to the driving frequency f0, the electromagnetic force generated by the drive coil 114 in the handle housing 105 acts on the transducer 130 to cause the transducer 130 in a resonant vibration state. It is well known that the energy transfer efficiency in the resonance oscillation state or the resonant vibration state is very high. In an existing driver configuration using a bearing (e.g., a ball bearing), a restraining piece such as a bearing is provided to prevent other motions of the cleaning device in addition to its rotary motion, however, such a constraint will bring noise and energy loss, while also increasing the cost. In the present invention, due to the reasonable configuration of the elastic elements and the permanent magnets, it is possible to achieve a smooth running of the transducer 130, thus eliminating some of the restraining pieces (such as bearings, etc.) that must be provided in order to achieve the rotation of the cleaning appliance. Since the reasonable configuration of the permanent magnet causes the electromagnetic resultant force on the transducer 130 to be approximately zero, and the torque acting on the transducer 130 is handily used so that the restraining structure can be removed, the cleaning appliance has a more compact structure, smoother rotation, and weaker noise. Furthermore, compared with the structure in which only one transducer elastic element is provided, the structure of the cleaning appliance according to the present invention has a weaker noise and higher efficiency.

When current passes through the left primary winding 120 of the drive coil 114, but does not pass through the right primary winding 121 of the drive coil 114, the secondary winding 128 of the drive coil 114 generates an induced electromotive force, and the secondary winding 128 of the drive coil 114 forms a closed loop with the external circuit, and therefore, the secondary winding 128 of the drive coil 114 also generates an induced current I1. When current does not pass through the left primary winding 120 of the drive coil 114 but passes through the right primary winding 121 of the drive coil 114, the secondary winding 128 of the drive coil 114 generates an induced current I2. By reasonably setting the circuit, it is possible to cause the currents I1 and I2 to be identical in frequency, opposite in direction and approximately equal to each other in magnitude.

Naturally, the skilled in this art can also work out other solutions, for example, the primary windings 120 and 121 of the drive coil 114 are eliminated so that the alternating current of a frequency f0 generated in the circuit directly passes through the secondary winding 128 of the drive coil 114, or only one primary winding is employed in the drive coil and an alternating current of a frequency f0 flows through the primary winding of the drive coil so that an induced current occurs in the secondary winding 128 of the drive coil, and so on. These solutions all do not go beyond the scope of the present invention.

Figure 5:
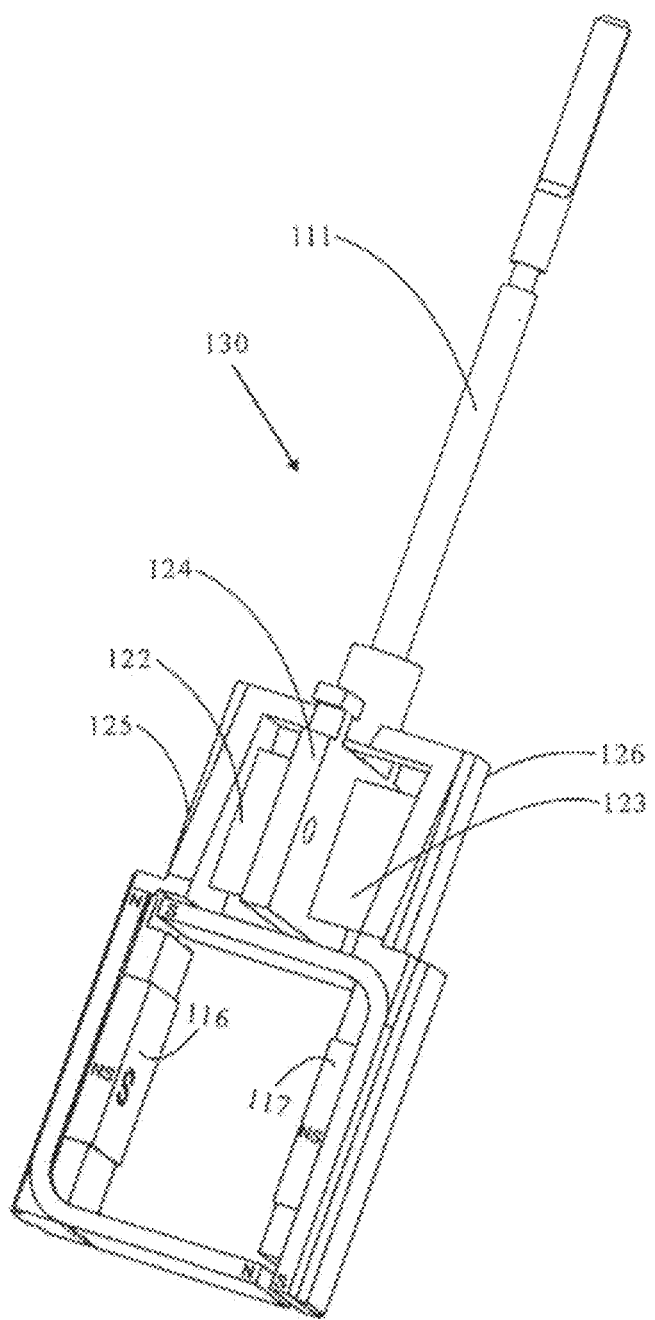
FIG. 5 is a perspective view of the transducer.
Figure 6:
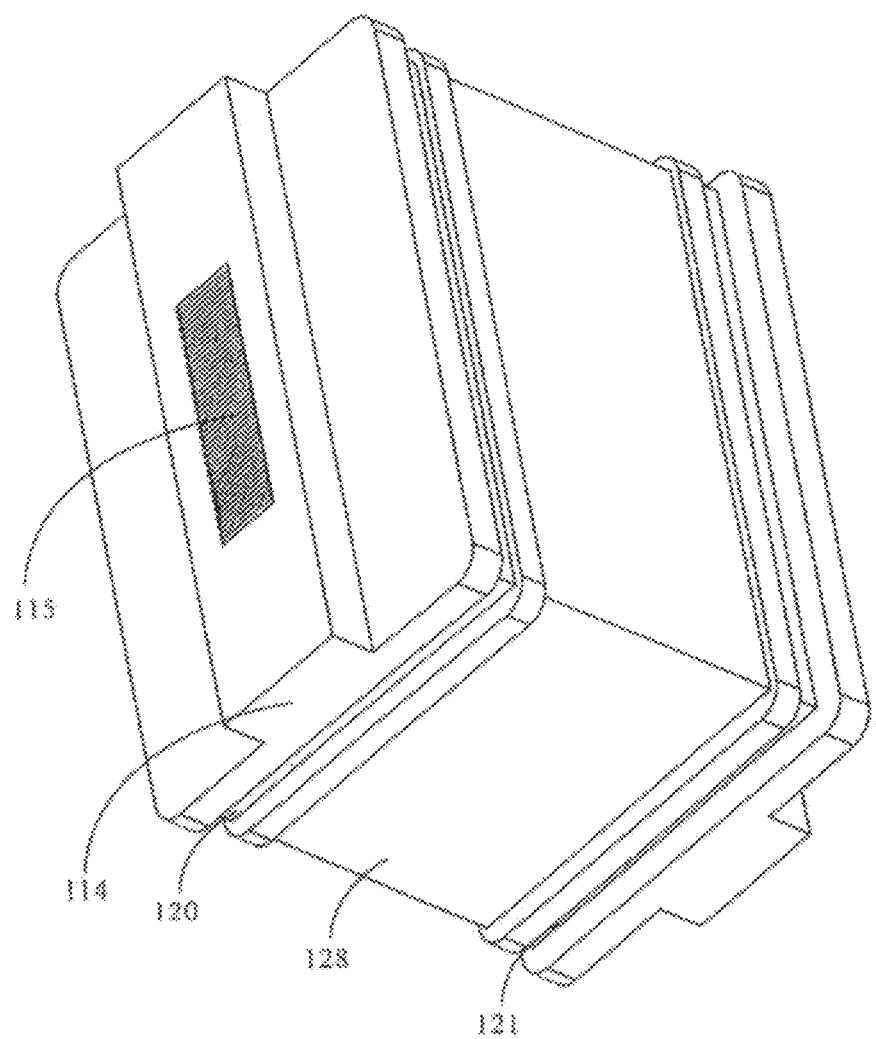
FIG. 6 is a perspective view of the drive coil shown in FIG. 4.
Figure 7:
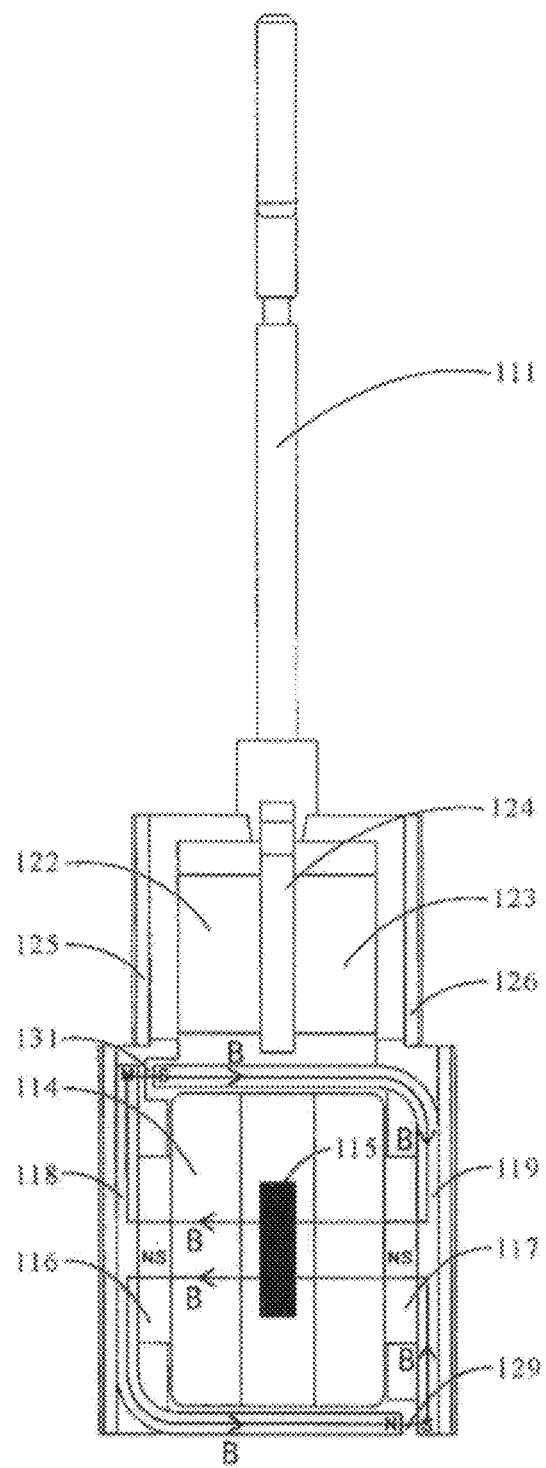
FIG. 7 is a schematic view of the combined transducer and drive coil.

Further as shown in FIGS. 5, 6, 7 and 8A, in this case, two movable and mutually independent left and right permanent magnets 116, 117 are distributed at both sides along the longitudinal axis of the drive shaft. The magnetic poles of the two permanent magnets 116, 117 in the direction toward the drive coil 114 are opposite to each other in polarity. The left and right permanent magnets 116, 117 may be arranged so that the angle between the direction of their inner magnetic line and the direction of the longitudinal axis of the drive coil iron core 115 is greater than 45° and less than 135°, and preferably, this angle is 90°. As shown in FIG. 7, the direction of the longitudinal axis of the drive coil iron core 115 is an inward or outward direction perpendicular to the paper surface, by this time, the direction of the longitudinal axis of the drive coil iron core 115 and the longitudinal axis of the drive shaft are orthogonal to each other.

In the present invention, the left and right permanent magnets 116, 117 are arranged such that, when the direction of their inner magnetic line and the direction of the longitudinal axis of the drive coil iron core 115 forms an angle of 90°, the direction of the magnetic line passing through the drive coil formed between the left and right permanent magnets 116, 117 and the direction of the magnetic line within the coil formed by the energized drive coil intersect spatially at 90°, that is to say, the axis of the magnetic field generated by the drive coil 114 and the axis of the permanent magnetic field are orthogonal to each other. The orthogonality of the above two magnetic fields can be understood as the fact that the two magnetic fields do not interfere with each other; when the magnitude and direction of the current in the drive coil 114 varies, the magnetic field generated by the drive coil 114 will change correspondingly; however, due to the orthogonality of the axis of the magnetic field of the drive coil 114 to the axis of the permanent magnetic field, the magnetic field variation generated by the drive coil 114 does not affect the permanent magnetic field. When alternating current passing through the drive coil 114 varies according to cosine, due to the energized conductor being in the magnetic field of the permanent magnet, the energized conductor is subjected to the electromagnetic force, and the electromagnetic force formula is $F=NBIL \cos \omega t$, where B is the magnetic field density of the permanent magnetic field at the conductor; $I \cos \omega t$ is the current flowing through the conductor; L is the effective length of the conductor in the permanent magnetic field; N is the total number of the conductor; $\omega$ is the electrical angular speed at which the current varies; t is time. It is known from the electromagnetic force formula that, if N, B, and L keep unchanged, then F merely depends on $I \cos \omega t$. In this case, the above orthogonal magnetic fields can ensure that B does not change, and the internal structure of the cleaning appliance can also ensure that N and L keep unchanged. Since the $\cos \omega t$ curve is a smooth curve, that is to say, the electromagnetic force is a continuous gradient physical quantity without an abrupt change, thereby ensuring that the cleaning appliance achieves a smooth non-impact motion under the driving of the electromagnetic force F, that is, the acceleration of the object motion has no abrupt change.

Figure 8A:
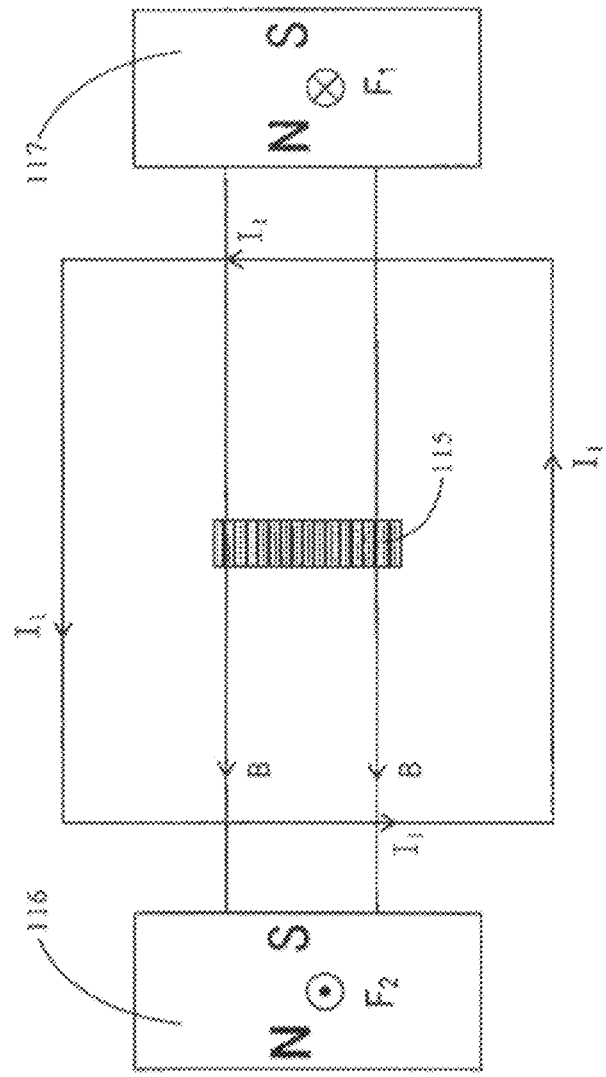
FIG. 8A is a principle explanatory drawing of the direction of current in the secondary winding of the drive coil and the direction of the force acting on the permanent magnet shown in FIG. 7.
Figure 8B:
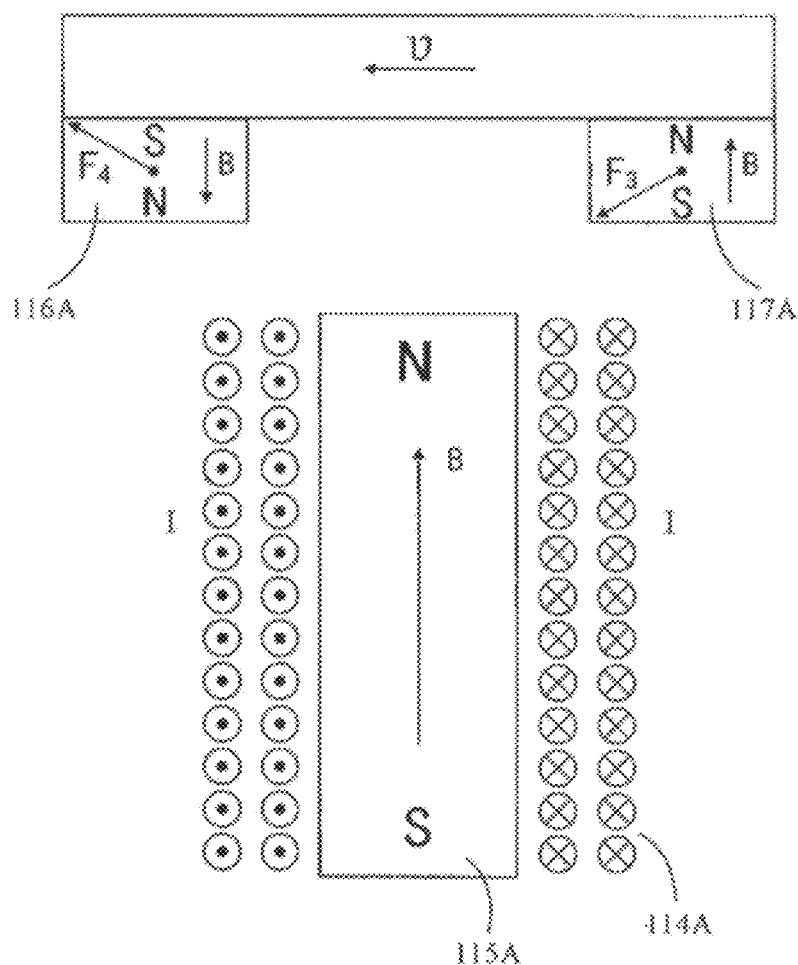
FIG. 8B is a principle explanatory drawing of the magnetic field force of the drive coil and the permanent magnet.

In order to analyze the advantages of the above orthogonal magnetic fields even more clearly, the case where the axis of the magnetic field of the permanent magnet and the axis of the magnetic field of the drive coil 114 are parallel to or coincide with each other is specifically analyzed through FIG. 8B.

As shown in FIG. 8, the permanent magnets are distributed above the drive coil 114A such that the direction of the magnetic line within the permanent magnets is parallel with the direction of the longitudinal axis of the drive coil iron core 115A (which is directed to the upward or downward direction along the paper surface as shown in FIG. 8B), by this time, the direction of the longitudinal axis of the drive coil iron core 115A and the longitudinal axis of the drive shaft are parallel with each other. Then the axis of the magnetic field generated by the drive coil 114A is parallel with the axis of the magnetic field of the permanent magnet; the magnetic field generated by the drive coil 114A and the magnetic field of the permanent magnet interfere with each other, and the magnitude and direction of the magnetic field generated by the drive coil 114A varies with the magnitude and direction of the current flowing through the drive coil 114A. The mutual interference between the two magnetic fields causes the magnetic field in the air gap between the permanent magnets and the drive coil 114A to be malformed with time, so that the magnetic field density B in the air gap is distorted, resulting in asymmetry of the magnetic field density B on both sides of the longitudinal axis of the drive shaft. Since the magnitude of the magnetic field density B affects the magnitude of the electromagnetic force, the magnetic field of the permanent magnet and the magnetic field of the drive coil 114A that interfere with each other can cause unbalanced forces on the left and right permanent magnets, which in turn causes the transducer of the cleaning appliance to produce translation in addition to its rotary motion, thereby resulting in noise and inefficiency of the cleaning appliance. In addition, there is also a magnetic field force of the magnetic poles between the magnetic pole of the drive coil iron core 115A and the magnetic pole of the permanent magnet, and such a magnetic field force may be attractive or repulsive. According to the theory of electromagnetism, the magnetic field force is inversely proportional to the square of the distance between the permanent magnet and the drive coil iron core 115A. As shown in FIG. 8B, the left permanent magnet 116A moves leftward under the action of the magnetic field force F4; the distance between the permanent magnet and the drive coil iron core 115A becomes larger, thus the magnetic field force F4 becomes less; and the right permanent magnet 117A moves leftward under the action of the magnetic field force F3; the distance between the permanent magnet and the drive coil iron core 115A becomes smaller, thus the magnetic field force F3 becomes larger. It will be apparent that the changes in F4 and F3 will result in a component force in the direction parallel with the longitudinal axis of the drive coil iron core 115A, and this component force is an alternating quantity, thereby causing vibration, noise and energy loss of the transducer of the cleaning appliance in the longitudinal axis direction of the drive coil iron core 115A.

In addition, the alternating magnetic field generated by the drive coil 114A continuously performs magnetizing and demagnetizing processes of the permanent magnets 116A and 117A. As shown in FIG. 8B, the left permanent magnet 116A is in a demagnetized state, and the right permanent magnet 117A is in a magnetized state. In the magnetizing and demagnetizing processes of the permanent magnets 116A and 117A, the permanent magnets 116A and 117A would produce magnetic hysteresis loss due to magnetic hysteresis effect, and such a magnetic hysteresis loss causes energy lost and thereby reduces the efficiency of the cleaning appliances. Furthermore, such magnetizing and demagnetizing effect places a higher demand on the material and properties of the permanent magnets 116A and 117A, and according to electromagnetic theory, when the magnetic intensity of the demagnetization is greater than the coercive force of the permanent magnet, the permanent magnet will be demagnetized and thus lose its magnetism; therefore, in applications where the axis of the magnetic field generated by the drive coil 114A is parallel to or overlaps with the axis of the magnetic field of the permanent magnet, the coercive force of the permanent magnet is greater than the magnetic intensity generated by the drive coil 114A, thereby restricting the selection of the permanent magnets 116A, 117A and the drive coil 114A.

As compared to the arrangement in which the axis of the magnetic field of the permanent magnet is parallel to or overlaps with the axis of the magnetic field of the drive coil 114A, in the example of the present invention, the arrangement of the axis of the magnetic field of the permanent magnet being orthogonal to the axis of the magnetic field of the drive coil 114 can overcome the above drawbacks, so that the cleaning appliance has a higher efficiency and can move even more smoothly and without impact, and at the same time, the range of choice for the permanent magnets 116, 117 and the drive coil 114 is widened.

Preferably, the permanent magnets 116, 117 may be made of NdFeB permanent magnet having a length of 5 to 30 mm, a width of 2 mm to 20 mm, and a height of 1 mm to 10 mm.

As shown in FIGS. 4, 6 and 8A, assuming that the current passing through the secondary winding 128 of the drive coil is I1, the direction of current is as shown in FIG. 8A. The left permanent magnet 116 is subjected to a reaction force outwardly perpendicular to the paper surface, and the right permanent magnet 117 is subjected to a reaction force inwardly perpendicular to the paper surface. When the drive coil 114 is not energized, the axis of the left transducer elastic element 122 along the transducer elastic element retainer 124 toward the direction of the left transmission arm 125 of the transducer is parallel to the direction of the magnetic line within the left permanent magnet 116. Similarly, the axis of the right transducer elastic element 123 along the transducer elastic element retainer 124 toward the direction of the right transmission arm 126 of the transducer is parallel to the direction of the magnetic line within the right permanent magnet 117. In this example, the left and right transducer elastic elements 122, 123 are parallel with each other and are in the same plane.

In the present invention, the left permanent magnet 116 and the left transducer elastic element 122 are formed as a vibrating system by the above structure, and when the left permanent magnet 116 is subjected to a reaction force in a direction outwardly perpendicular to the paper surface, the left permanent magnet 116 tends to move in the direction outwardly perpendicular to the paper surface. The left permanent magnet 116 is constrained by the left transducer elastic element 122. When the left transducer elastic element 122 is subjected to a force or component force in the direction inwardly or outwardly perpendicular to the paper surface, or is subjected to an upward or downward moment along the direction of the paper surface, at a region close to the left transmission arm 125 of the transducer, the left transducer elastic element 122 generates a bending deflection around the boundary line of the left transducer elastic element 122 and the transducer elastic element retainer 124 as an axis. In this case, it is preferable that the left transducer elastic element 122 is disposed so that the turning angle corresponding to the deflection of the left transducer elastic element 122 is less than 10°. Therefore, when the left permanent magnet 116 is subjected to a reaction force in the direction outwardly perpendicular to the paper surface, the left permanent magnet 116 moves in the direction outwardly perpendicular to the paper surface and conforming the deflection motion law of the left transducer elastic element 122. It can also be understood that the left permanent magnet 116 moves in the direction outwardly perpendicular to the paper surface, and the movement direction is approximately parallel to the direction of the longitudinal axis of the drive coil iron core 115, that is, their angle is greater than 170° and less than or equal to 180°, or alternatively, greater than −10° and less than or equal to 0°.

Similarly, when the right permanent magnet 117 is subjected to a reaction force inwardly perpendicular to the paper surface, and the right permanent magnet 117 tends to move in the direction inwardly perpendicular to the paper surface. The right permanent magnet 117 is constrained by the right transducer elastic element 123. When the right transducer elastic element 123 is subjected to a force or component force in the direction inwardly or outwardly perpendicular to the paper surface, or is subjected to an upward or downward moment along the direction of the paper surface, at the region close to the right transmission arm 126 of the transducer, the right transducer elastic element 123 generates a bending deflection around the boundary line of the right transducer elastic element 123 and the transducer elastic element retainer 124 as an axis. In this case, it is preferable that the right transducer elastic element 123 is disposed so that the turning angle corresponding to the deflection of the right transducer elastic element 123 is less than 10°. Therefore, when the right permanent magnet 117 is subjected to a reaction force in the direction inwardly perpendicular to the paper surface, the right permanent magnet 117 moves in the direction inwardly perpendicular to the paper surface and conforming the deflection motion law of the right transducer elastic element 123. It can also be understood that the right permanent magnet 117 moves in the direction inwardly perpendicular to the paper surface, and the movement direction is approximately parallel to the direction of the longitudinal axis of the drive coil iron core 115 (i.e., in the direction inwardly or outwardly perpendicular to the paper surface as shown in FIG. 7), that is, their angle is greater than or equal to 180° and less than 190°, or alternatively, greater than or equal to 0° and less than 10°.

Obviously, when the direction of current flowing through the drive coil 114 is opposite to that shown in FIG. 8A, the movement directions of the left and right permanent magnets 116, 117 are opposite to each other; the left permanent magnet 116 moves in the direction inwardly perpendicular to the paper surface, and its movement direction is approximately parallel with the direction of the longitudinal axis of the drive coil iron core 115, and the angle thereof is greater than or equal to 180° and less than 190°, or alternatively, greater than or equal to 0° and less than 10°. The right permanent magnet 117 moves in the direction outwardly perpendicular to the paper surface, and its movement direction is approximately parallel with the direction of the longitudinal axis of the drive coil iron core 115, and the angle thereof is greater than 170° and less than or equal to 180°, or alternatively, greater than −10° and less than or equal to 0°.

In summary, when a alternating current of frequency f0 passes through the secondary winding 128 of the drive coil 114, the permanent magnets 116 and 117 are subjected to reaction force from the drive coil 114 to move, and the movement directions of the left and right permanent magnets 116 and 117 are approximately parallel with the direction of the longitudinal axis of the drive coil iron core 115, that is, the angle thereof is greater than 170° and less than 190°, or alternatively, greater than −10° and less than 10°. Obviously, it is also possible to use permanent magnet distribution mode different from the present example.

Figure 9:
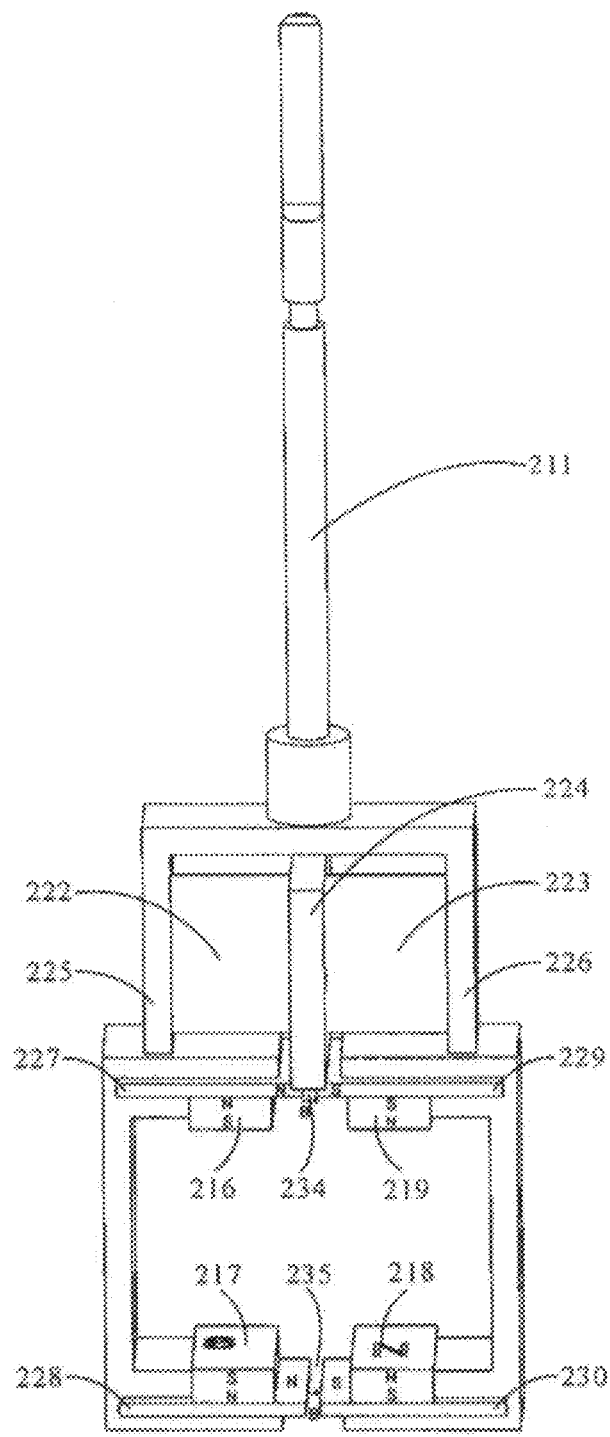
FIG. 9 is a perspective view of the first variant of transducer.
Figure 10:
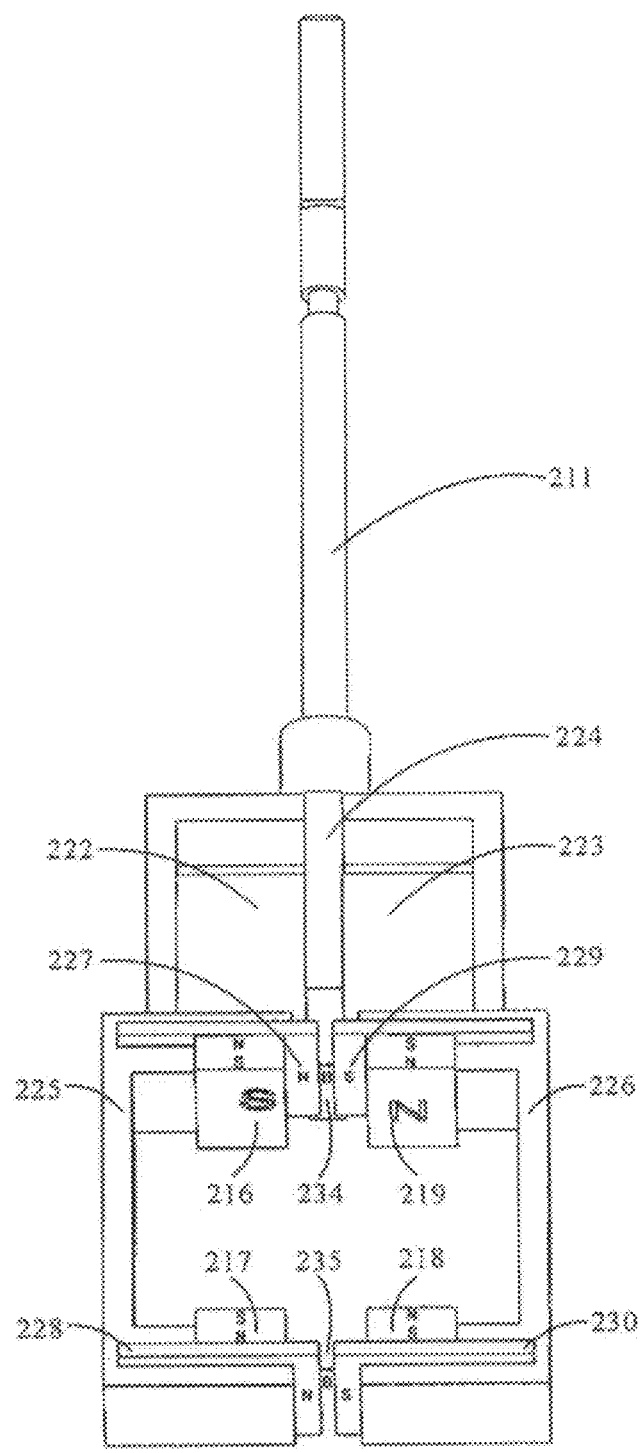
FIG. 10 is a perspective view of the transducer shown in FIG. 9 seen from another angle.
Figure 11A:
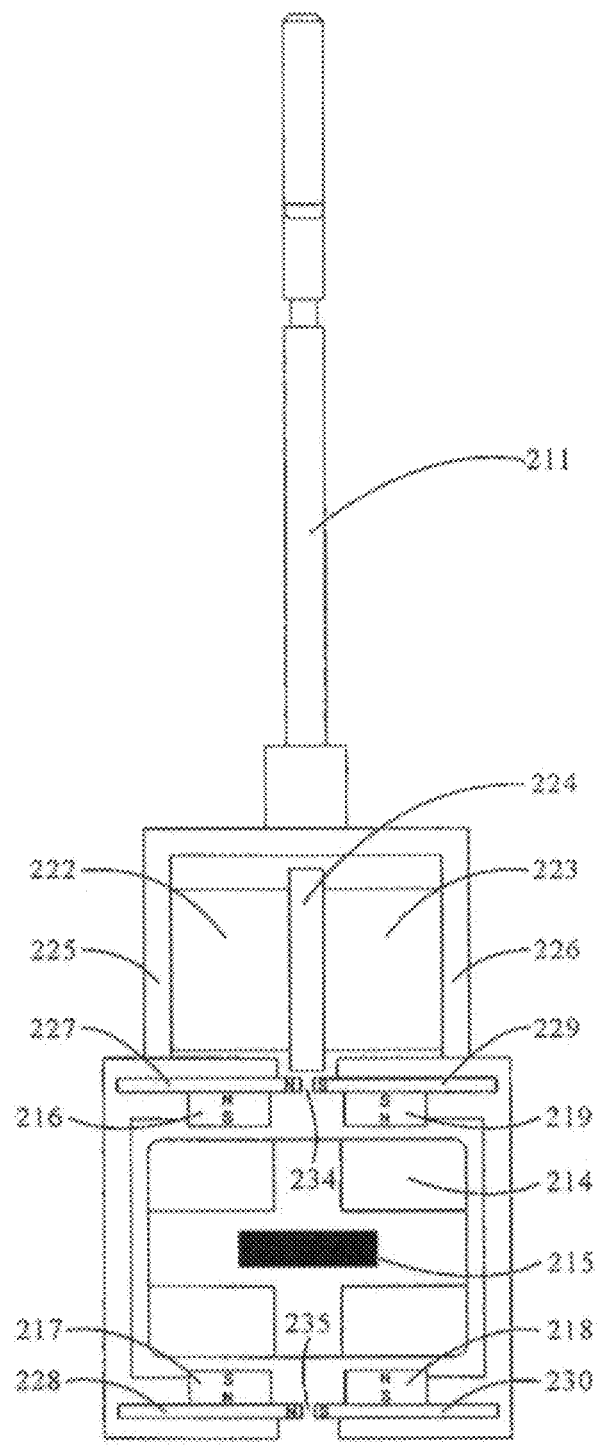
FIG. 11A is a schematic view of the combined transducer shown in FIG. 9 and an alternative drive coil.

In another embodiment, as shown in FIGS. 9, 10, 11A, the first variant of transducer is provided with four permanent magnets 216, 217, 218, 219 which are fixedly coupled to respective permanent magnet brackets 227, 228, 229, 230. The permanent magnet brackets 227, 228, 229, 230 are made of highly magnetic permeable materials, such as industrial pure iron or silicon steel sheet or the like. The first variant of transducer comprises permanent magnets 216, 217, 218, 219 of the first variant of transducer, upper and lower left permanent magnet brackets 227, 228 of the first variant of transducer, upper and lower right permanent magnet brackets 229, 230 of the first variant of transducer, the left and right transmission arms 225, 226 of the first variant of transducer, the left and right transducer elastic elements 222, 223 of the first variant of transducer, the transducer elastic element retainer 224 for the first variant of transducer, and the drive shaft 211 of the first variant of transducer; these parts are fixedly coupled together.

In this embodiment, the polarity of the magnetic pole the upper left permanent magnet 216 of the first variant of transducer in the direction toward the drive coil 114 is S pole, and the polarity of the magnetic pole of the lower left permanent magnet 217 of the first variant of transducer in the direction toward the drive coil 114 is S pole; the polarity of the magnetic pole of the upper right permanent magnet 219 of the first variant of transducer in the direction toward the drive coil 114 is N pole, and the polarity of the magnetic pole of the lower right permanent magnet 218 of the first variant of transducer in the direction toward the drive coil 114 is N pole. The permanent magnets 216, 217, 218, 219 of the first variant of transducer are movable relative to the transducer elastic element retainer 224 for the first variant of transducer. Naturally, the configuration of these permanent magnets can also have many other solutions, for example, the polarity of the magnetic pole of the right permanent magnets 219 and 218 in the direction toward the drive coil 114 is S pole, and the polarity of the magnetic pole of the left permanent magnets 216 and 217 in the direction toward the drive coil 114 is N pole, and so on.

The portion of the first variant of transducer, in which the left transmission arm 225 of the first variant of transducer, the upper left permanent magnet bracket 227 of the first variant of transducer, the lower left permanent magnet bracket 228 of the first variant of transducer, the upper left permanent magnet 216 of the first variant of transducer and the lower left permanent magnet 217 of the first variant of transducer are fixedly coupled, and which is below the left transducer elastic element 222, is referred to as the lower left portion of the first variant of transducer. The portion of the first variant of transducer, in which the right transmission arm 226 of the first variant of transducer, the upper right permanent magnet bracket 229 of the first variant of transducer, the lower right permanent magnet bracket 230 of the first variant of transducer, the upper right permanent magnet 219 of the first variant of transducer and the lower right permanent magnet 218 of the first variant of transducer are fixedly coupled, and which is below the right transducer elastic element 223, is referred to as the lower right portion of the first variant of transducer. At least one gap exists between the lower left portion of the first variant of transducer and the lower right portion of the first variant of transducer, and this gap may allow at least one left permanent magnet of the first variant of transducer (e.g., the permanent magnet 217) to move relative to a right permanent magnet having opposite polarity (e.g., the permanent magnet 218).

Figure 11B:
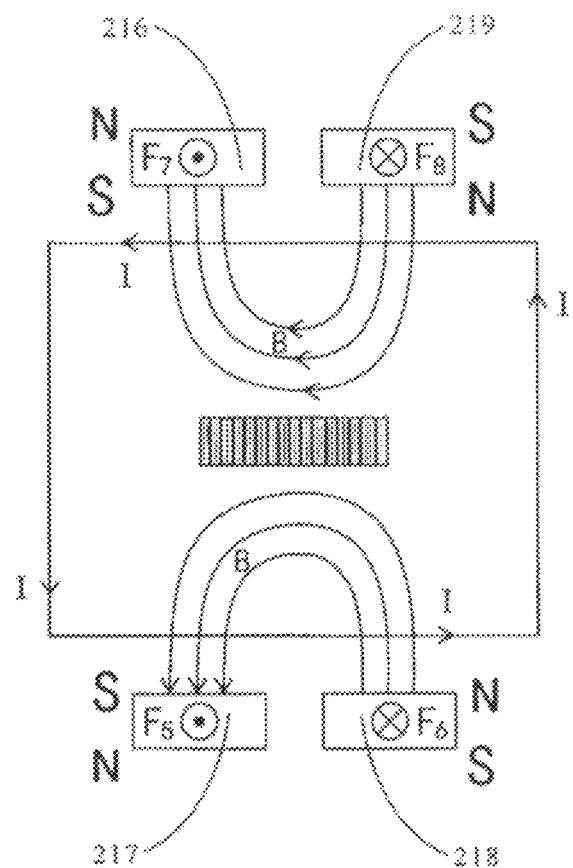
FIG. 11B is a principle explanatory drawing of the direction of current in the secondary winding of the drive coil and the direction of the force acting on the permanent magnet shown in FIG. 11A.
Figure 12:
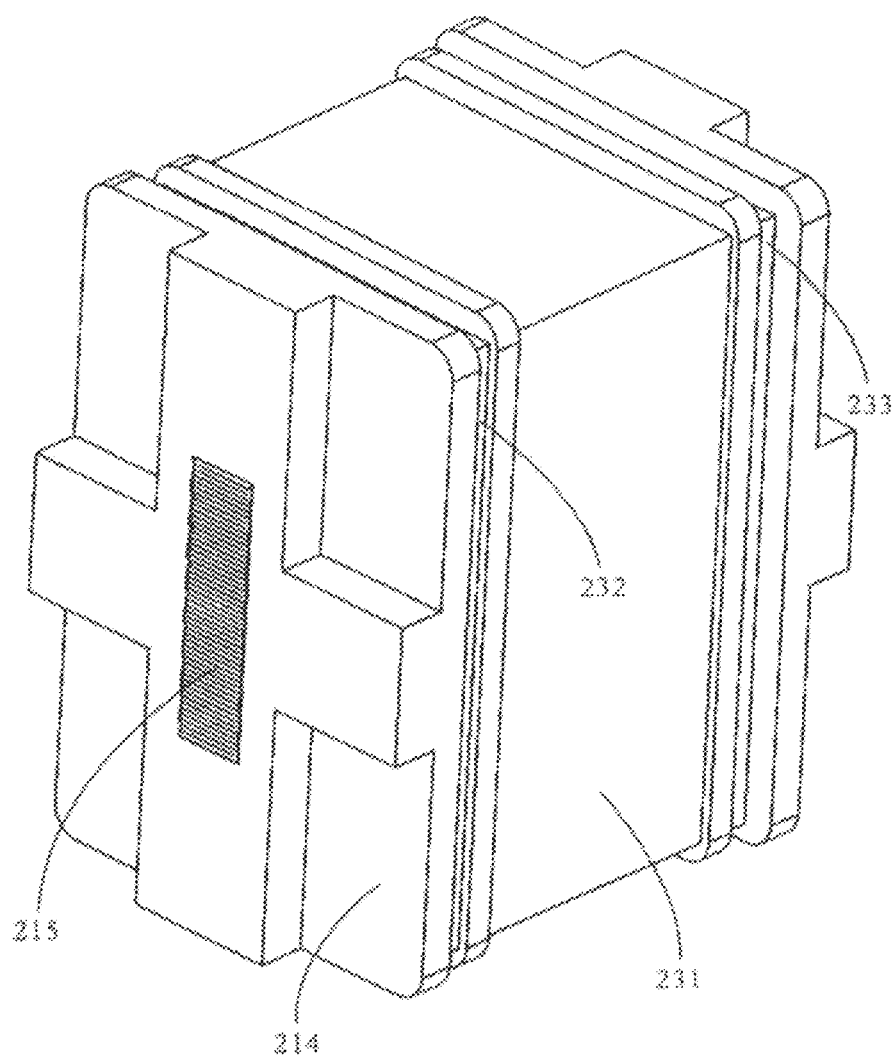
FIG. 12 is a perspective view of the alternative drive coil shown in FIG. 11A.

In this embodiment, two gaps 234, 235 exist between the lower left portion of the first variant of transducer and the lower right portion of the first variant of transducer. These gaps allow at least one left permanent magnet (e.g., the permanent magnet 217) and at least one right permanent magnet having opposite polarity (e.g., the permanent magnet 218) to be independent from each other. It can also be understood that, there are four moveable permanent magnets on both sides of the longitudinal axis of the drive shaft, among the four moveable permanent magnets and in the direction toward the drive coil 114, at least one left permanent magnet (e.g., the permanent magnet 217) has its polarity of the magnetic pole opposite to the polarity of the magnetic pole of one right permanent magnet (e.g., the permanent magnet 218). At least one left permanent magnet (e.g., the permanent magnet 217) is independent from one right permanent magnet having opposite polarity (e.g., the permanent magnet 218), and it can also be understood that at least one left permanent magnet (e.g., the permanent magnet 217) can move relative to the right permanent magnet having opposite polarity (e.g., the permanent magnet 218). FIG. 11A is a schematic view of the combination of the first variant of transducer and the alternative drive coil; FIG. 11B is an explanatory drawing of the direction of current in the secondary winding of the drive coil and the direction of the force acting on the permanent magnet as shown in FIG. 11A. The placement manner of the permanent magnets is different from that shown in FIGS. 1-7. As shown in FIGS. 11A and 11B, since the permanent magnet brackets 227, 228, 229, 230 of the first variant of transducer are made of highly magnetic permeable materials, the magnetoresistance of the permanent magnet bracket of the first variant of transducer is small, and most of the flux of the permanent magnet flows through the permanent magnet brackets. According to the magnetic field theory, the upper left permanent magnet bracket 227 of the first variant of transducer forms an N magnetic pole on the plane facing the gap 234, and the upper right permanent magnet bracket 229 of the first variant of transducer forms a S magnetic pole on the plane facing the gap 234, so that the N magnetic pole of the upper left permanent magnet bracket 227 of the first variant of transducer facing the gap 234 and the S magnetic pole of the upper right permanent magnet bracket 229 of the first variant of transducer facing the gap 234 generate a magnetic field force, and this magnetic field force is attractive, and the characteristic of this magnetic field force is that the length of the magnetic line in the gap 234 is kept the shortest.

Due to the manufacturing errors or other interference, the magnetic field forces F6, F8 and F5, F7 shown in FIGS. 11A and 11B are not equal in magnitude, and thus the equilibrium condition of the forces received by the transducer of the cleaning appliance is destroyed; such a transducer experiencing non-equilibrium forces will produce a translation tendency in addition to its rotary motion, thereby losing energy and generating noise; however, the gaps 234 and 235 in this example can effectively correct such an unbalanced force. Assuming F8>F7, F6>F5, then the inward force acting on the right side of the transducer of the cleaning appliance is greater than the outward force acting on the left side of the transducer of the cleaning appliance. The upper right permanent magnet bracket 229 of the first variant of transducer moves inwardly relative to the upper left permanent magnet bracket 227 of the first variant of transducer, so that the length of magnetic line in the gap 234 is made longer; due to the fact that magnetic field force generated by the upper right permanent magnet bracket 229 of the first variant of transducer and the upper left permanent magnet bracket 227 of the first variant of transducer and present in the gap 234 tends to maintain the magnetic line to be shortest, thus the magnetic field force will react against the motion induced by the inward unbalanced force, and generate an outward magnetic field force acting on the upper right permanent magnet bracket 229 of the first variant of transducer, and thereby the magnetic field force in the gap 234 corrects the motion generated by the unbalanced force, that is, the magnetic field force tends to maintain the relative position of the upper right permanent magnet bracket 229 of the first variant of transducer and the upper left permanent magnet bracket 227 of the first variant of transducer unchanged, so that the cleaning appliance moves more stably. The magnitude of the magnetic field force in the gap 234 determines its degree of response to the unbalanced force; according to the theory of electromagnetism, the effective volume of the magnetic field in the gap 234 affects the magnitude of the magnetic field force, and it can also be said that the length of the gap 234 affects the magnitude of the magnetic field force. At the same time, the magnetic intensity of the permanent magnet also affects the magnitude of the magnetic field force.

A large quantity of experiments show that the length of the gap 234 is preferably between 0.1 mm and 2 mm, and more preferably, the length of the gap is 0.2 mm to 1 mm. The gap 235 has the same function and the same principle. Similarly, as shown in FIGS. 4, 5, 7 and 13, the upper gap 131 between the lower left portion of the transducer 130 and the lower right portion of the transducer and the lower gap 129 between the lower left portion of the transducer 130 and the lower right portion of the transducer have the same function as that of the gaps 234 and 235, and the upper gap 332 between the lower left portion of the second variant of transducer and the lower right portion of the transducer and the lower gap 333 between the lower left portion of the second variant of transducer and the lower right portion of the transducer have the same function as that of the gaps 234 and 235, which is not detailed here.

As shown in FIG. 11B, similar to the analysis of the transducer 130, in the alternative drive coil 214 of the first variant of transducer, there are four moveable permanent magnets 216, 217, 218 and 219 distributed on both sides of the longitudinal axis of the drive shaft, and at least one left permanent magnet (e.g., the permanent magnet 217) and one right permanent magnet having opposite polarity of the magnetic pole (e.g., the permanent magnet 218) are independent from each other. The two movable and mutually independent permanent magnets 217 and 218 are opposite in their respective polarity in the direction toward the alternative drive coil 214; the two movable and mutually independent permanent magnets 217 and 218 are subjected to reaction force from the alternative drive coil 214 so as to move, and the movement direction of the left and right permanent magnets 217, 218 is approximately parallel to the direction of the longitudinal axis of the alternative drive coil iron core 215 (i.e., in the direction inwardly or outwardly perpendicular to the paper surface as shown in FIG. 11A), that is, the angle thereof is greater than 170° and less than 190°, or greater than −10° and less than 10°.

Naturally, there can be a variety of positional distribution for the transducer permanent magnets, for example, the position and quantity of the permanent magnets in the transducer 130 and the first variant of transducer may be arbitrarily combined, and none of these solutions goes beyond the scope of the present invention.

As shown in FIGS. 4, 5 and 7, the transducer elastic elements 122, 123 preferably comprise rectangular elastic elements or sheet type elastic elements.

As shown in FIGS. 4, 5 and 7, in the example of transducer 130, the left and right transducer elastic elements 122, 123 are rectangular parallelepiped metal elastic sheets; both ends of the left and right transducer elastic elements 122, 123 are respectively fixedly coupled to the transducer elastic element retainer 124 and the left and right transmission arms 125, 126 of the transducer; the left transducer elastic element 122 carries the motion and energy from the left permanent magnet 116, and the right transducer elastic element 123 carries the motion and energy from the right permanent magnet 117. In this example, the transducer elastic element retainer 124 is fixed in the handle 1, and the left and right transmission arms 125, 126 of the transducer can move in accordance with the deflection law of the elastic elements with respect to the transducer elastic element retainer 124. The left and right transmission arms 125, 126 of the transducer are fixedly coupled to the above of the transducer elastic elements 122, 123 and are fixedly coupled to the drive shaft 111; the cleaning element 3 is fixedly coupled onto the cleaning element carrier 2, and the cleaning assembly is detachably connected onto the drive shaft 111. A person skilled in this art can design a reasonable structure of the drive shaft 111 and the cleaning assembly, so that the drive shaft 111 effectively drives the cleaning assembly. When the movable and mutually independent permanent magnets 116 and 117 are moved by the reaction force from the drive coil 114, the transducer elastic elements 122 and 123 move with the motion of the permanent magnets 116 and 117, and the transducer elastic elements 122, 123 continue to absorb and release energy; when the response frequency of the transducer elastic elements 122, 123 and the current frequency of the drive coil 114 are close to each other, the energy conversion efficiency of the transducer is significantly improved, and the entire electric toothbrush is in a high efficiency state. Since the motion of the left permanent magnet 116 is constrained by the left transducer elastic element 122, when the left permanent magnet 116 is subjected to a reaction force approximately parallel to the longitudinal axis of the drive coil iron core 115, the left transmission arm 125 and the left permanent magnet 116 of the transducer make a bending motion around the boundary line between the transducer elastic element retainer 124 and the left transducer elastic element 122 as an axis; likewise, the right transmission arm 126 and the right permanent magnet 117 of the transducer make a bending motion around the boundary line between the transducer elastic element retainer 124 and the right transducer elastic element 123 as an axis. The longitudinal axis of the drive shaft 111 is approximately parallel to the boundary line between the transducer elastic elements 122, 123 and the transducer elastic element retainer 124; more preferably, the angle between the longitudinal axis of the drive shaft 111 and the boundary line is greater than or equal 0° and less than 15°, and the shortest distance from the longitudinal axis of the drive shaft 111 to the left transducer elastic element 122 is the same as the shortest distance from the longitudinal axis of the drive shaft 111 to the right transducer elastic element 123.

In the illustrated example, the magnitudes of the reaction forces received by the left permanent magnet 116 and the right permanent magnet 117 are approximately equal; preferably, their magnitude difference is less than about 10%; the directions thereof are approximately opposite, and the angle between the directions thereof is less than 10°; the left transducer elastic element 122 and the right transducer elastic element 123 are approximately equal in their lengths and their bending resistant section factors (or section modulus in bending) respectively, preferably, the magnitude difference is less than 10%; thus, the deflection magnitudes of the left transducer elastic element 122 and the right transducer elastic element 123 are approximately equal, and the magnitude difference is less than 10, and the respective deflection directions are opposite. Therefore, the drive shaft 111 is subjected to an approximately alternating equilibrium force, and such an alternating equilibrium force produces an alternating torque, creating a high-speed reciprocating and high effective rotation of the drive shaft 111. In a similar way, the first variant of transducer and the second variant of transducer may also obtain similar effects.

Figure 14:
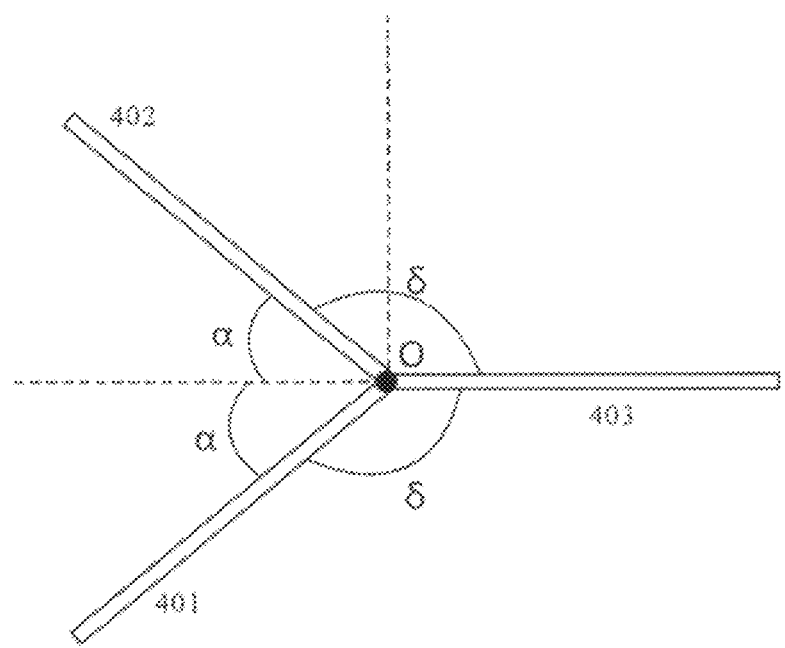
FIG. 14 is a schematic view of the combination of alternative transducer elastic elements.

According to the present invention, the number of the transducer elastic elements may be plural. As shown in FIG. 14, three transducer elastic elements 401, 402, 403 can be disposed, in which the angle of two transducer elastic elements, e.g., the transducer elastic elements 401 and 402, is $2\alpha$, $0°<\alpha<90°$, and any one of the two transducer elastic elements 401, 402 and the third transducer elastic element 403 form an angle $\delta$, $\delta=(360°-2\alpha)/2$.

As shown in FIGS. 4, 5, 7 and 14, by rational configuration of the bending resistant section factor (or section modulus in bending) and length of the elastic elements 401, 402, 403, it is possible to make the magnitude of the force acting on the driver shaft by the left and right transmission arms of the transducer approximately equal; preferably, the magnitude difference of the forces acting on the driver shaft by the left and right transmission arms 125, 126 of the transducer is less than 10%, and the forces are opposite in direction, and the moments of the left and right transmission arms 125, 126 with respect to the longitudinal axis of the drive shaft have approximate magnitudes; preferably, the magnitude difference of the moments of the left and right transmission arms 125, 126 of the transducer with respect to the longitudinal axis of the drive shaft is less than 10, and the directions of the moments are identical, thereby achieving the effect that the driver shaft drives the cleaning element carrier 2 and the cleaning element 3 to reciprocally rotate smoothly and in a high speed.

Figure 13:
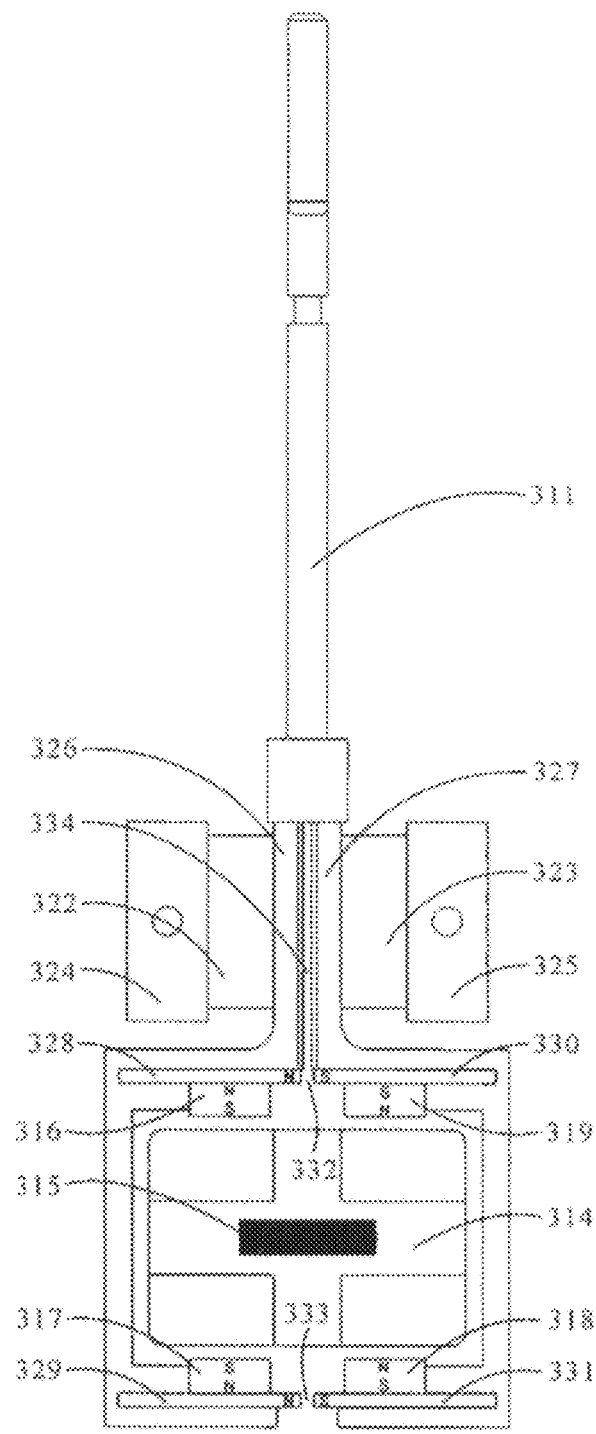
FIG. 13 is a schematic view of the combination of the second variant of transducer and another alternative drive coil.

FIG. 13 illustrates the second variant of transducer, which differs from the transducer shown in FIG. 7 and the first variant of transducer shown in FIG. 9 in that, in the embodiments shown in FIGS. 7 and 9, a single elastic retainer 124 or 224 is provided, and compared with the distances of the left transmission arm 125 or 225 of the transducer and the right transmission arm 126 or 226 of the transducer from the axis of the drive shaft 111 or 211, the single transducer elastic element retainer 124 is closer to the axis of the drive shaft 111; while in the example of FIG. 13, two elastic retainers are provided, namely the left transducer elastic retainer 324 and the right transducer elastic retainer 325, and compared with the distances of the left transmission arm 326 of the transducer and the right transmission arm 327 of the transducer from the axis of the driver shaft 311 respectively, these two elastic retainers 324, 325 are further away from the axis of the driver shaft 311. Absolutely, regardless of the number of the transducer elastic element retainers being provided, the common feature of these structures is that at least two transducer elastic elements are distributed on both sides of the longitudinal axis of the drive shaft 111, 211 or 311, and one end of the permanent magnet and one end of the transducer elastic element on the same side of the longitudinal axis of the drive shaft 111, 211 or 311 are coupled with each other. The transmission arm of the transducer elastic element is movable relative to the corresponding transducer elastic element retainer, and at least one pair of transmission arms of the transducer elastic element are provided on both sides of the longitudinal axis of the drive shaft. The angle of the movement directions of said pair of transmission arms of the transducer elastic element is greater than 90° and less than 270°. Accordingly, as long as the shape and position of the permanent magnet and the shape and position of the transducer elastic element are reasonably designed, and further, the bending resistant section factor (or section modulus in bending) and torsion resistant section factor (or section modulus in torsion) of the elastic element are reasonably designed, it is possible to achieve a high efficient motion of the cleaning devices, and can expand the range of choice for the physical dimensions of the transducer elastic elements.

What is claimed is:
1. A personal cleaning care appliance, comprising:
a handle comprising a handle housing, a power supply portion for supplying power to respective portions of the personal cleaning care appliance, a control portion for controlling the various operation modes of the personal cleaning care appliance and the opening or closing of the personal cleaning care appliance, a trigger portion for turning on or off an operation of the personal cleaning care appliance, and a driver for converting input electrical energy into output mechanical energy, wherein the power supply portion, the control portion, the trigger portion, and the driver are provided inside the handle housing, wherein the driver comprises a transducer, a drive coil, a drive coil iron core arranged in the drive coil, and a left driver bracket and a right driver bracket for supporting the driver;
a cleaning assembly comprising a cleaning element carrier and cleaning elements distributed on the cleaning element carrier;
wherein the transducer comprises a drive shaft inserted into the cleaning assembly and detachably connected to the cleaning assembly, transducer elastic element retainer fastened to the left and right driver brackets, at least two permanent magnets disposed on left and right sides with respect to a longitudinal axis of the drive shaft, corresponding permanent magnet brackets for fixedly connecting the permanent magnets, left and right transducer transmission arms fixedly connected to the permanent magnet brackets and to the drive shaft, and left and right transducer elastic elements respectively disposed on the left and right sides of the longitudinal axis of the drive shaft; the longitudinal axis of the drive shaft is approximately parallel to the boundary line between the transducer elastic elements and the transducer elastic element retainer with the angle therebetween being greater than or equal 0° and less than 15°, one end of the left transducer elastic element and one end of the right transducer elastic element are fixedly connected to the transducer elastic element retainers respectively, and the other end of the left transducer elastic element and the other end of the right transducer elastic element are fixedly connected to the corresponding transducer transmission arms respectively, wherein the left and right permanent magnets are independent from each other; a polarity of a magnetic pole of the permanent magnet at one side in a direction toward the drive coil is S pole or N pole; a polarity of a magnetic pole of the permanent magnet at the other side in a direction toward the drive coil is opposite to the polarity of the magnetic pole of the permanent magnet at the one side; the left and right permanent magnets are arranged such that an angle between a direction of their inner magnetic line and a direction of a longitudinal axis of the drive coil iron core is greater than 45° and less than 135° respectively; the left and right permanent magnets are movable relative to the transducer elastic element retainers; when an alternating current passing through the drive coil has a frequency f0, the movement direction of the left and right permanent magnets is approximately parallel with the direction of the longitudinal axis of the drive coil iron core, that is, the angle therebetween is greater than 170° and less than 190°, or greater than −10° and less than 10°.

2. The personal cleaning care appliance according to claim 1, wherein the left and right permanent magnets are arranged such that the angle between the direction of their inner magnetic line and the direction of the longitudinal axis of the drive coil iron core is 90°.

3. The personal cleaning care appliance according to claim 2, wherein the left and right permanent magnets are rectangular parallelepiped NdFeB permanent magnets being 5 mm to 30 mm in length, 2 mm to 20 mm in width, and 1 mm to 10 mm in height.

4. The personal cleaning care appliance according to claim 2, wherein the transducer is provided with four permanent magnets, and the left permanent magnets and right permanent magnets are arranged such that the reaction forces which they are subjected to are of approximately equal magnitude and the directions of the reaction forces are approximately opposite; the magnitude difference of the reaction forces is less than 10%, and the angle between the directions of the reaction forces is less than 10°.

5. The personal cleaning care appliance according to claim 1, wherein the transducer elastic elements are two transducer elastic elements distributed symmetrically at the left and right sides of the longitudinal axis of the drive shaft, and the two transducer elastic elements form an angle of 180°, wherein the left transducer elastic element and the right transducer elastic element are provided in such a way that the left transducer elastic element and the right transducer elastic element are approximately equal in their length and their bending resistant section factor respectively with a magnitude difference less than 10%, such that a deflection of the left transducer elastic element and a deflection of the right transducer elastic element have approximately equal magnitudes with a magnitude difference less than 10%, and are opposite in directions.

6. The personal cleaning care appliance according to claim 2, wherein the transducer elastic element are two transducer elastic elements distributed symmetrically at the left and right sides of the longitudinal axis of the drive shaft, and the two transducer elastic elements form an angle of 180°, wherein the left transducer elastic element and the right transducer elastic element are provided in such a way that the left transducer elastic element and the right transducer elastic element are approximately equal in their length and their bending resistant section factor respectively with a magnitude difference less than 10%, such that a deflection of the left transducer elastic element and a deflection of the right transducer elastic element have approximately equal magnitudes with a magnitude difference less than 10%, and are opposite in directions.

7. The personal cleaning care appliance according to claim 2, wherein the transducer is provided with three transducer elastic elements, in which two of the transducer elastic elements form an angle $2\alpha$, $0°<\alpha<90°$, and either of the two transducer elastic elements and the third transducer elastic element forms an angle $\delta$, $\delta=(360°-2\alpha)/2$.

8. The personal cleaning care appliance according to claim 2, wherein the personal cleaning care appliance comprises an electric toothbrush, an electric shaver, an electric face cleansing instrument, and an electric shower.

9. The personal cleaning care appliance according to claim 1, wherein a portion of the transducer, in which the left transmission arm, the left permanent magnet located at the same side as the transmission arm with respect to the longitudinal axis of the drive shaft, and the corresponding permanent magnet bracket are in fixed connection, and which is below the left transducer elastic element located at the same side as the transmission arm with respect to the longitudinal axis of the drive shaft, is defined as a lower left portion of the transducer; a portion of the transducer, in which the right transmission arm, the right permanent magnet and the corresponding permanent magnet bracket are in fixed connection, and which is below the right transducer elastic element, is defined as a lower right portion of the transducer; at least one gap exists between the lower left portion of the transducer and the lower right portion of the transducer; in the gap there exits a magnetic field force sufficient to compensate for a translation of the transducer due to non-equilibrium forces, and at least one permanent magnet is allowed to move relative to the other permanent magnet having the opposite polarity.

10. The personal cleaning care appliance according to claim 9, wherein the gap between the lower left portion of the transducer and the lower right portion of the transducer has a length of 0.1 mm to 2 mm.

11. The personal cleaning care appliance according to claim 9, wherein the gap between the lower left portion of the transducer and the lower right portion of the transducer has a length of 0.2 mm to 1 mm.

12. The personal cleaning care appliance according to claim 9, wherein the left and right permanent magnets are rectangular parallelepiped NdFeB permanent magnets being 5 mm to 30 mm in length, 2 mm to 20 mm in width, and 1 mm to 10 mm in height.

13. The personal cleaning care appliance according to claim 9, wherein the transducer is provided with four permanent magnets, and the left permanent magnets and right permanent magnets are arranged such that the reaction forces which they are subjected to are of approximately equal magnitude and the directions of the reaction forces are approximately opposite; the magnitude difference of the reaction forces is less than 10%, and the angle between the directions of the reaction forces is less than 10°.

14. The personal cleaning care appliance according to claim 2, wherein the left and right transducer elastic elements comprise rectangular elastic elements or sheet type elastic elements.

15. The personal cleaning care appliance according to claim 9, wherein the left and right transducer elastic elements comprise rectangular elastic elements or sheet type elastic elements.

16. The personal cleaning care appliance according to claim 9, wherein the transducer elastic elements are two transducer elastic elements distributed symmetrically at the left and right sides of the longitudinal axis of the drive shaft, and the two transducer elastic elements form an angle of 180°, wherein the left transducer elastic element and the right transducer elastic element are provided in such a way that the left transducer elastic element and the right transducer elastic element are approximately equal in their length and their bending resistant section factor respectively with a magnitude difference less than 10%, such that a deflection of the left transducer elastic element and a deflection of the right transducer elastic element have approximately equal magnitudes with a magnitude difference less than 10%, and are opposite in directions.

17. The personal cleaning care appliance according to claim 9, wherein the transducer is provided with three transducer elastic elements, in which two of the transducer elastic elements form an angle $2\alpha$, $0°<\alpha<90°$, and either of the two transducer elastic elements and the third transducer elastic element forms an angle $\delta$, $\delta=(360°-2\alpha)/2$.

18. The personal cleaning care appliance according to claim 9, wherein the personal cleaning care appliance comprises an electric toothbrush, an electric shaver, an electric face cleansing instrument, and an electric shower.

19. The personal cleaning care appliance according to claim 1, wherein the left and right permanent magnets are rectangular parallelepiped NdFeB permanent magnets being 5 mm to 30 mm in length, 2 mm to 20 mm in width, and 1 mm to 10 mm in height.

20. The personal cleaning care appliance according to claim 1, wherein the transducer is provided with four permanent magnets, and the left permanent magnets and right permanent magnets are arranged such that the reaction forces which they are subjected to are of approximately equal magnitude and the directions of the reaction forces are approximately opposite; the magnitude difference of the reaction forces is less than 10%, and the angle between the directions of the reaction forces is less than 10°.

21. The personal cleaning care appliance according to claim 1, wherein the left and right transducer elastic elements comprise rectangular elastic elements or sheet type elastic elements.

22. The personal cleaning care appliance according to claim 1, wherein the transducer is provided with three transducer elastic elements, in which two of the transducer elastic elements form an angle $2\alpha$, $0°<\alpha<90°$, and either of the two transducer elastic elements and the third transducer elastic element forms an angle $\delta$, $\delta=(360°-2\alpha)/2$.

23. The personal cleaning care appliance according to claim 1, wherein the personal cleaning care appliance comprises an electric toothbrush, an electric shaver, an electric face cleansing instrument, and an electric shower.

\* \* \* \* \*